US006858007B1

United States Patent
Akselrod et al.

(10) Patent No.: US 6,858,007 B1
(45) Date of Patent: Feb. 22, 2005

(54) METHOD AND SYSTEM FOR AUTOMATIC CLASSIFICATION AND QUANTITATIVE EVALUATION OF ADNEXAL MASSES BASED ON A CROSS-SECTIONAL OR PROJECTIONAL IMAGES OF THE ADNEX

(75) Inventors: Solange Akselrod, Givat Shumel (IL); Ron Tepper, Hertzlia (IL); Yair Zimmer, Tel Aviv (IL)

(73) Assignee: Ramot University Authority For Applied Research and Industrial Development Ltd., Tel Aviv (IL)

( * ) Notice: Subject to any disclaimer, the term of this patent is extended or adjusted under 35 U.S.C. 154(b) by 0 days.

(21) Appl. No.: 09/444,672

(22) Filed: Nov. 22, 1999

(30) Foreign Application Priority Data

Nov. 25, 1998 (IL) ................................................ 127254

(51) Int. Cl.⁷ ................................................ A61B 8/00
(52) U.S. Cl. ........................ 600/437; 100/443; 100/445; 100/448; 128/916; 382/128; 382/286
(58) Field of Search ................................ 382/199, 128, 382/264, 266, 286; 600/443, 445, 448, 437; 128/916

(56) References Cited

U.S. PATENT DOCUMENTS 5,421,330 A * 6/1995 Thirion et al.
5,457,754 A * 10/1995 Han et al.
5,799,100 A * 8/1998 Clarke et al.
5,850,836 A * 12/1998 Steiger et al.
5,904,652 A * 5/1999 Gilbert et al. .............. 600/447
5,970,164 A * 10/1999 Bamberger et al.
5,984,870 A * 11/1999 Giger et al.
6,112,108 A * 8/2000 Tepper et al. ............... 600/407

OTHER PUBLICATIONS

Zimmer et al, "An Improved Method to Compute the Convex Hull of a Shape in a Binary Image", *Pattern Recognition*, 30(3): 397–402, 1997.
Zimmer et al, "The Distribution of the Local Entropy in Ultrasound Images", *Ultrasound in Med. & Biol.*, 22(4): 431–439, 1996.
Zimmer et al, "A Two–Dimensional Extension of Minimum Cross Entropy Threshholding for the Segmentation of Ultrasound Images", *Ultrasound in Med. & Biol.*, 22(9): 1183–1190, 1996.

* cited by examiner

Primary Examiner—Marvin M. Lateef
Assistant Examiner—Jeoyuh Lin
(74) Attorney, Agent, or Firm—G.E. Ehrlich Ltd.

(57) ABSTRACT

A method of characterizing an adnexal mass is disclosed, the method is effected by (a) obtaining a cross-sectional or projectional image of an examined adnex including the adnexal mass; (b) extracting boundaries of the adnexal mass; and (c) using a first algorithm for quantifying at least one morphological feature of the adnexal mass, thereby providing quantification of the at least one morphological feature.

13 Claims, 7 Drawing Sheets

$k_1(i,j)$ $k_2(i,j)$

 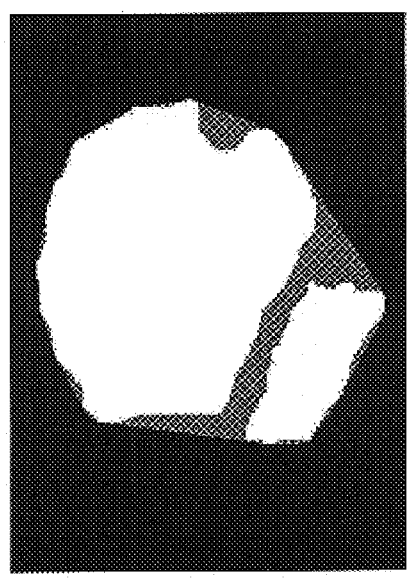
Fig. 8a    Fig. 8b
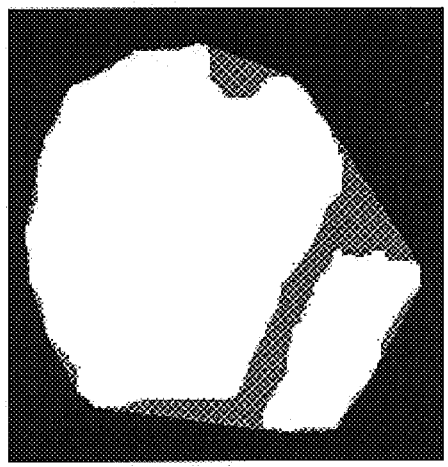 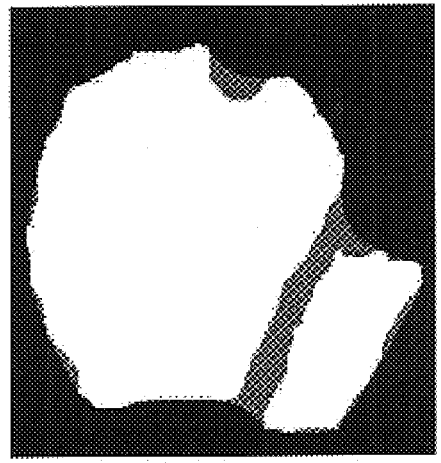
Fig. 9a    Fig. 9b
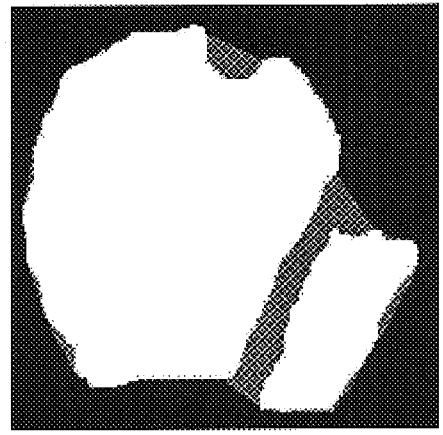
Fig. 9c

METHOD AND SYSTEM FOR AUTOMATIC CLASSIFICATION AND QUANTITATIVE EVALUATION OF ADNEXAL MASSES BASED ON A CROSS-SECTIONAL OR PROJECTIONAL IMAGES OF THE ADNEX

FIELD AND BACKGROUND OF THE INVENTION

The present invention relates to a method and system for classification and quantitative evaluation of masses, and more particularly, to a method and system for automatic, and therefore objective, classification and quantitative evaluation of adnexal masses based on cross-sectional or projectional images of the adnex.

As used herein in the specification and in the claims section hereinunder, the terms "adnex" and "adnexal" refer to the pelvic gynecological adnex, which is also known in the art as the uteral adnex, including the ovary and the fallopian tubes complex.

Ovarian masses are a common phenomenon among women of all ages. The necessity to find an efficient way for classifying ovarian masses and detecting malignant tumors is evident, especially considering the high mortality rate due to ovarian cancer and the difficulty in detecting a tumor in the early stages of the disease. In order to quantitatively assess the malignancy of an ovarian pathology, it is common to score several properties of the ovarian mass (obtained from ultrasound images) according to a pre-determined table, and to use the resulting value for classification. Currently, no existing scoring system is based on either automatic or semi-automatic image analysis.

Major types of ovarian masses: Cysts are the most common ovarian pathology. Most of them are benign, however some cysts are malignant. An ovarian cyst is formed when part of the ovary is filled with fluid while the ovarian tissue is compressed to the remaining volume. Since the fluid within the cyst is not echogenic, while the ovarian tissue is echogenic, the cyst in its simplest form appears in an ultrasound image as a dark region encircled by bright pixels. Cysts, however, are usually more complicated and are typically characterized by several features. To start with, the fluid within the cyst may be clear or turbid. Cysts may also contain small regions of ovarian tissue penetrating from the cyst's boundary into its volume. Such projections are called papillations. The thickness of the wall, i.e., the layer between the cyst and the external ovarian boundary (containing ovarian tissue), is also an important parameter. The cyst may be divided into several parts to form a multilocular cyst by septations, which are narrow stripes of ovarian tissue. These septations can be either complete (thus forming several separated cystic lumens) or incomplete. The size of the cyst and the regularity (i.e., smoothness) of its wall are also important for diagnosis.

Solid masses are another class of ovarian pathologies. Although some of them are benign (e.g., solid teratoma, fibroma), many of them are malignant. Contrary to cysts, solid masses appear as lumps of echogenic (i.e., bright) material within the ovary. Important parameters besides their size are the homogeneity (as appears in the ultrasound image) of the solid material, and the presence of echogenic foci (small very bright spots). Solid masses are less detectable than cysts because of the low contrast between the mass and its surroundings. There are cases in which the ovarian mass encompasses a cyst and solid tissue. Such cases are defined as semi-solid masses, which are also known as complex masses.

The above partition of ovarian masses into three major types is used by Fleischer [1] for the sonographic differential diagnosis of pelvic masses. This partition, and the morphological features used for describing the mass are provided in Table 1, below.

TABLE 1

| Rough classification of ovarian masses | |
| --- | --- |
| Types of ovarian masses | Cyst, semi-solid, solid |
| Feature set | Echogenity (gray level) |
| | Wall structure (papillations) |
| | Septations |
| | Wall thickness |
| | Mass volume |
| | Echogenic foci |

Based on this set of characteristics, a detailed diagnosis of the mass (identifying the specific pathology and assessing its malignancy), is performed. Obviously, the full medical decision making process is based not only on the morphological features as observed in B-scan ultrasound images, but also on blood flow features as expressed by a Doppler signal (e.g., RI, PI), blood tests (e.g., checking the serum CA125 levels), the patient's history, and histological examination.

Scoring systems: A commonly used tool for malignancy detection in the ovary are scoring systems. The idea underlying the scoring system is to score several properties of the ovarian mass, according to a pre-determined table, and to use the resulting value (such as the sum of the individual scores) for classification. The scoring table usually provided a small number of different scores for each property, where the division to values is determined by commonly used criteria. Sassone et al. [2] designed a scoring system that includes four characteristics of the mass (the inner wall structure, the wall thickness, the presence and width of septa, and the echogenity of the region). Other scoring systems were suggested [3–6]. The scoring system discussed by DePriest et al. [5], for example, refers to the volume, the wall structure (smooth or including papillations), and the structure of the septa.

Although these scoring systems reasonably succeed in sorting the ovarian mass to either benign or malignant, they are based on subjective evaluations made by an operator. Despite the recent progress in image processing, no existing scoring system is currently based either on automatic or on semi-automatic analysis of images.

Automatic analysis of ovarian masses—current status: The major attempts to automatically analyze ovarian ultrasound images [7–12] referred only to ovarian follicles. A computerized system for quantification of ovarian masses, however, must deal with more complex ovarian morphology. Currently, no published research fully addresses this problem. A powerful tool in the area of medical diagnosis are expert systems. Brüning et al. [13] presented an expert system called ADNEXPERT, which is specifically designed to assist the sonographic diagnosis of adnexal tumors. However, the ADNEXPERT system provides differential diagnosis of adnexal masses based on classification data provided manually thereto by the physician. Thus, the ADNEXPERT system provides automation clearly limited to the final decision making step of mass evaluation.

There is thus a widely recognized need for, and it would be highly advantageous to have, a method and system for automatic classification and quantitative evaluation of adnexal masses based on cross-sectional or projectional images of the adnex, which provide an objective scoring system for adnexal masses.

SUMMARY OF THE INVENTION

According to one aspect of the present invention there is provided a method of characterizing an adnexal mass, the method comprising the steps of (a) obtaining a cross-sectional or projectional image of an examined adnex including the adnexal mass; (b) extracting boundaries of the adnexal mass; and (c) using a first algorithm for quantifying at least one morphological feature of the adnexal mass, thereby providing quantification of the at least one morphological feature.

According to further features in preferred embodiments of the invention described below, obtaining the cross-sectional or projectional image of the examined adnex is effected by a method selected from the group consisting of ultrasound, computerized tomography, X ray, positron emission tomography, magnetic resonance imaging, single photon emission computerized tomography and nuclear imaging.

According to still further features in the described preferred embodiments the ultrasound is selected from the group consisting of B scan ultrasound and Doppler ultrasound.

According to still further features in the described preferred embodiments extracting the boundaries of the adnexal mass is effected manually.

According to still further features in the described preferred embodiments extracting the boundaries of the adnexal mass is effected by a second algorithm.

According to still further features in the described preferred embodiments the second algorithm is selected from the group consisting of an edge extraction algorithm and a region extraction algorithm.

According to still further features in the described preferred embodiments the edge extraction algorithm is selected from the group consisting of an active contour model algorithm, such as, but not limited to, a snakes algorithm, a radial search algorithm and a contour following algorithm.

According to still further features in the described preferred embodiments the region extraction algorithm is selected from the group consisting of a region growing algorithm and a thresholding algorithm.

According to still further features in the described preferred embodiments the adnexal mass is selected from the group consisting of a cyst, a solid mass an a semi-solid mass.

According to still further features in the described preferred embodiments the first algorithm performs an initial classification of the adnexal mass to a cyst, a solid mass or a semi-solid mass.

According to still further features in the described preferred embodiments the at least one morphological feature of the adnexal mass is selected from the group consisting of size, volume, presence of papillations, presence of septations (either complete or incomplete septations), wall regularity, turbidity, homogeneity and echogenic foci.

According to still further features in the described preferred embodiments the method further comprising the step of (d) using the quantification of the at least one morphological feature of the adnexal mass in a scoring system for issuing a diagnosis related to the adnexal mass.

According to still further features in the described preferred embodiments the scoring system is effected by a second algorithm.

According to still further features in the described preferred embodiments the scoring system is effected manually.

According to another aspect of the present invention there is provided a system of characterizing an adnexal mass comprising (a) a first hardware for operating a first algorithm for obtaining a cross-sectional or projectional image of an examined adnex including the adnexal mass in a digitized form; (b) a second hardware for operating a second algorithm for quantifying at least one morphological feature of the adnexal mass, thereby providing quantification of the at least one morphological feature.

According to further features in preferred embodiments of the invention described below, the system further comprising a third hardware for operating a third algorithm for extracting boundaries of the adnexal mass.

According to still further features in the described preferred embodiments the system further comprising a third hardware for operating a scoring algorithm for issuing a diagnosis related to the adnexal mass based on the quantification of the at least one morphological feature of the adnexal mass.

The present invention successfully addresses the shortcomings of the presently known configurations by providing an automatic and therefore objective and effective tool for quantitatively characterizing features of adnexal masses.

BRIEF DESCRIPTION OF THE DRAWINGS

The invention herein described, by way of example only, with reference to the accompanying drawings, wherein:

FIG. 6a demonstrates a papillation; FIG. 6b demonstrates an incomplete septation; FIG. 6c demonstrates a complete septation; whereas FIG. 6d demonstrates an "internal" septation. In all cases, the structures are indicated by arrows.

FIGS. 8a–b show examples of the computed convex hull of a cyst as used with the algorithm according to the present invention used for automatic classification and quantitative evaluation of adnexal masses. FIG. 8a corresponds to the image of FIG. 6b, whereas FIG. 8b corresponds to the image of FIG. 6c. The images were magnified for display. In these Figures, the original cyst is shown in white and the convex deficiency is shown in gray.

FIGS. 9a–c demonstrate the process of correcting the convex deficiency used in accordance with the algorithm according to the present invention used for automatic classification and quantitative evaluation of adnexal masses. FIG. 9a shows the initial convex deficiency and is therefore identical to FIG. 8b; FIG. 9b shows the result obtained after morphological closing with a disc; whereas FIG. 9c shows the final result. The image was magnified for display.

FIG. 10a shows a square; FIG. 10b shows a horizontal line; FIG. 10c shows a vertical line; whereas FIGS. 10d–e show diagonal segments. The width of a septation was evaluated using the square, while the characteristic diameter of a papillation was assessed using the four structuring elements shown in FIGS. 10b–e.

DESCRIPTION OF THE PREFERRED EMBODIMENTS

Figure 1:
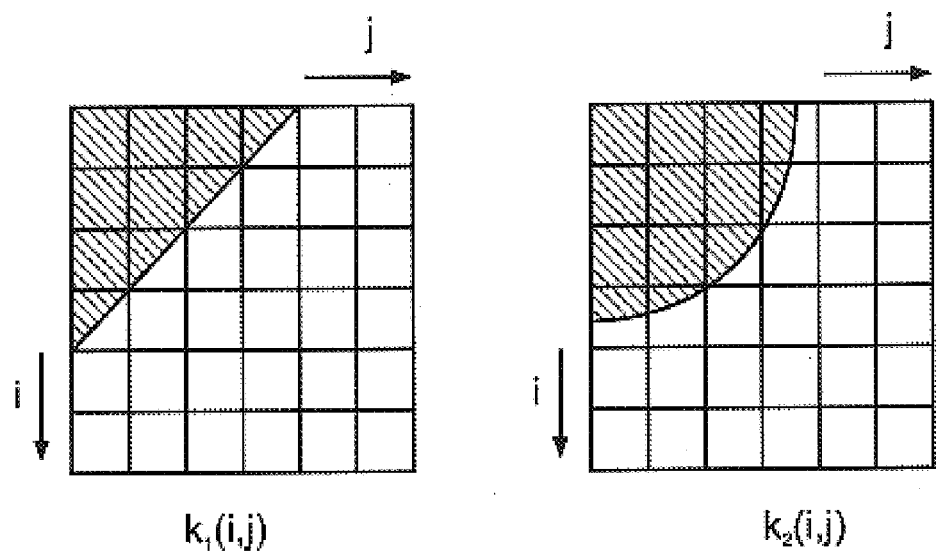
FIG. 1 is a scheme showing partition of a 2D parameter space by a specific value of K(i,j) according to a preferred segmentation algorithm employed by the present invention.

The present invention is of a method and system for automatic classification and quantitative evaluation of adnexal masses based on cross-sectional or projectional images of the adnex, which can be used for cancer diagnosis, treatment and prognosis. Specifically, the present invention can be used to provide an objective scoring tool for adnexal masses.

The principles and operation of a method and system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The detailed analysis of an adnexal mass according to the present invention includes several steps, such as, but not limited to, determining the boundaries of the mass, evaluating the dimensions of the mass, identifying various structures within the mass (if present) and quantitatively assessing their characteristics. The qualitative and quantitative data collected can be displayed or incorporated in a decision making procedure and thereby assist in decision making related to diagnosis, treatment and/or prognosis. In addition to improving differential diagnosis, the present invention can be used as a training tool for training and improving the skills of inexperienced users, and it can be combined to teleradiology systems.

According to the present invention, an automatic and quantitative analysis of adnexal masses using cross sectional, such as B-scan ultrasound, or projectional, such as X ray, images is presented. The method according to the present invention focuses on morphological classification and quantitative evaluations of the mass, yielding a feature set that quantitatively describes the morphology of the mass. This automatically obtained quantitative data can be used as an input for a scoring system to evaluate the malignancy of the mass. The innovation of the present invention lies mainly in the quantitative morphological analysis, because neither existing scoring systems nor currently available expert systems perform this task automatically.

Thus, as explained above, the gist of the present invention is quantitative morphological analysis of adnexal masses which is performed by implementing two major steps (i) initial classification of the mass; and (ii) detailed analysis thereof. The first step basically categorizes the mass into one of the three major tumor types (cyst, semi-solid, solid), based on the statistical properties of the mass. In this step, one defines a set of parameters (statistical and structural), presents them in a feature space, and categorizes the mass using decision rules. The second step is a detailed (i.e., quantitative) morphological analysis of the mass. In this latter step, different processing chains are applied to the image, depending on the former initial classification. Initially, the already extracted information of the mass is further analyzed for refined classification. This sub-step enables, for example, separating transparent cysts from turbid ones, and allows to identify some specific tumors of clinical importance. Then, a specific (i.e., suitable) algorithm for detailed analysis is applied on each tumor according to its type.

For solid masses and some pre-identified specific masses (e.g., endometrioma), typically the mass size (volume) has to be evaluated in order to provide for adequate diagnosis. For semi-solid masses, the size, composition (relative parts of solid and cystic materials), and the structure of the cystic parts must be evaluated. The latter item is essentially addressed using an algorithm designed for analyzing cysts. This algorithm, which is described in detail below, extracts the quantitative information characterizing the cyst.

The above algorithm is typically applied on a single two-dimensional ultrasonic image, however other image types are envisaged as further detailed hereinunder. In order to extract 3D information about the tumor (e.g., volume), a series of consecutive cross-sectional images can be obtained and analyzed. Integrating the data from the different images provides the required 3D information. Furthermore, it enables to correct evaluation errors in a specific image using the data obtained from the other images in the set.

The final step in the analysis is malignancy evaluation, which is performed based on the collected data and the criteria provided either manually or by commonly used scoring systems.

Thus, according to the present invention there is provided a method of characterizing an adnexal mass. The method according to the present invention is implemented either fully automatically or semi-automatically by first obtaining a cross-sectional or projectional image of an examined adnex which includes the adnexal mass. Thereafter, the boundaries of the adnexal mass are extracted either manually or preferably automatically as further detailed hereinunder and as exemplified in Example 1 of the examples section below. Subsequently, an algorithm is employed for quantifying at least one morphological feature of the adnexal mass, thereby providing quantification of the at least one morphological feature of the mass. A non-limiting example of the latter algorithm is provided in Examples 2–5 of the Examples section that follows.

As used herein in the specification and in the claims section below, the term "morphological feature" refers both to features characterizing the mass as a whole, such as, for example, size or volume, and further to features of more localized nature, such as, for example, septations and papillations.

The cross-sectional or projectional image of the examined adnex can be obtained according to the present invention by any imaging device, including, but not limited to, ultrasound (both B scan ultrasound and Doppler ultrasound), computerized tomography, single photon emission computerized tomography, X ray, positron emission tomography, magnetic resonance imaging and nuclear imaging, and by various methods including the use of contrast agents. The ordinary artisan is well familiar with these imaging methods, which are therefore not further described herein. A general text book relating to imaging methods in general and adnexal imaging in particular is [35].

As already mentioned, extracting the boundaries of the adnexal mass can be effected manually by an expert accustomed at interpreting cross-sectional and/or projectional images of the adnex. However, according to a preferred embodiment of the present invention, extracting the boundaries of the adnexal mass is effected by a region extraction algorithm which identifies and isolates the area located within a specified object in the image [30, 36], and an edge extraction algorithm which identifies and isolates the edge of a specified object in the image [30, 36]. Examples of presently preferred edge extraction algorithms include, but are not limited to, active 5 contour models (including snakes algorithms), in which an initial contour is iteratively changed until it overlays the actual desired edge [37], radial search algorithms, in which a series of rays is sent from a center point within the analyzed image object in many directions and a set of points that belong to the desired edge of this object are collected and used to reconstruct the entire contour [38], and contour following algorithms, which start from an initial point of the contour and proceed from one point to the neighboring one, according to pre-defined criteria, until the entire contour is identified [30, 36]. Examples of region extraction algorithms include, but no limited to, region growing algorithms which start from an initial area within the analyzed image object and gradually enlarge the area identified as belonging to the object until the entire object is identified [36], and thresholding algorithms in which the gray level (or another feature's) histogram of the image is divided into at least two sub-ranges according to a threshold (or thresholds) and the image pixels related to each sub-range are differently marked (separating, for example, objects from background) [39]. An example of the efficiency and operation of the latter algorithm is provided in Example 1 of the Examples section and in reference [15] of the references list enclosed herewith.

According to a preferred embodiment of the present invention the adnexal mass is selected from the group consisting of a cyst, a solid mass an a semi-solid mass and the quantifying algorithm performs an initial classification of the adnexal mass to a cyst, a solid mass or a semi-solid mass. This step is relatively straight forward, especially if ultrasound is employed since the echogenity of cysts, solid and semi-solid masses results in clearly distinguishable image results According to another preferred embodiment of the present invention the quantified morphological feature of the adnexal mass is selected from the group consisting of size (in cross section), volume (if successive cross sections are obtained), presence of papillations (e.g., number of and width), presence of septations (e.g., number of and width), wall regularity, turbidity (in ultrasound—small scatterers), homogeneity and echogenic foci. Each of these features characterized one or more of the cyst, solid and semi-solid mass types and quantitative analysis thereof is therefore preferably first correlated with the mass type. Thus, according to a preferred embodiment of the invention the quantifying algorithm has dedicated routes for analyzing each of these masses.

According to still further features in the described preferred embodiments the method further comprising the step of (d) using the quantification of the at least one morphological feature of the adnexal mass in a scoring system for issuing a diagnosis related to the adnexal mass.

For full automation, the method according to the present invention preferably further includes an automated scoring system, effected by a scoring algorithm, as described, for example, in reference [13]. However, scoring according to the present invention can also be performed manually [2–6]. In any case, scoring results in an indication related to the diagnosis of the mass, for example, whether the mass is malignant or benign. As used herein in the specification and in the claims section that follows, the term "scoring system" also refers to an expert system, as these terms are accepted in the art of computerized medical diagnostics.

Figure 12:
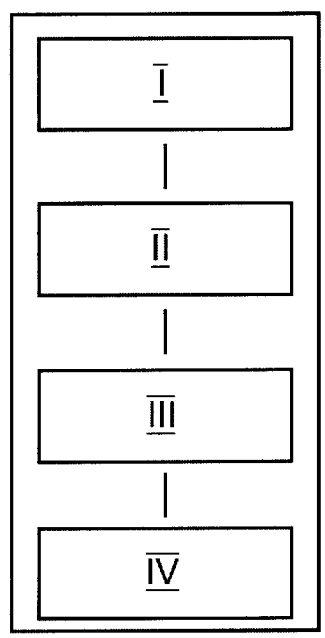
FIG. 12 is a schematic depiction of a system according to the present invention.

As shown in FIG. 12, according to another aspect of the present invention there is provided a system 10 for characterizing an adnexal mass. System 10 includes a first hardware I for operating a first algorithm for obtaining a cross-sectional or projectional image of an examined adnex including the adnexal mass in a digitized form. Such an algorithm is described in the Examples section hereinunder. System 10 further includes a second hardware II for operating a second algorithm for quantifying at least one morphological feature of the adnexal mass, thereby providing quantification of the at least one morphological feature. Preferably, system 10 further includes a third hardware III for operating a third algorithm for extracting boundaries of the adnexal mass.

According to a preferred embodiment of the present invention, system 10 further includes an additional hardware IV for operating a scoring algorithm for issuing a diagnosis (e.g., malignancy potential) related to the adnexal mass based on the quantification of the at least one morphological feature of the adnexal mass.

It will be appreciated by one ordinarily skilled in the art that any subset of hardwares I through IV or all of them can be integrated into a single hardware which typically includes a memory device and a processing device, which can perform, for example, image acquisition and display. A well known single hardware according to the present invention can be a personal computer (PC). Indeed, a personal computer was employed to operate the algorithms described hereinunder in the Examples section.

System 10 can therefore be used to implement the method according to the present invention hereinabove described and every one and all of the preferred embodiments thereof.

The immediate application of the method and system according to the present invention is routine use in differential diagnosis of ovarian masses, performed in hospitals and clinics. The algorithms described herein can be transformed into a software package, which can then be installed in commercial ultrasound scanners as part of their diagnostic analysis software. This software can be also installed on local PCs (or workstations) connected to an imager, hence enabling using it with a variety of currently available imagers.

There are also several future applications for the method and system according to the present invention. Since the algorithm is automatic, it can be used in teleradiology, screening of large populations (for early detection of ovarian cancer), and training and improving the skills of inexperienced users.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Defining Mass Boundaries

As mentioned hereinabove, numerous methods in image analysis pan be employed to define the boundaries of an image component which differs from its surroundings. This example describes a prior art process [15] which was successfully applied to define boundaries of ovarian cysts.

Segmentation is often an important step in the analysis of medical images. The gray value of a pixel is the most widely used variable for region segmentation. Other features, such as the local texture, can also be utilized for that purpose. The local entropy, however, is considered more suitable for boundary extraction. Nevertheless, in ultrasound images containing transparent fluid encircled by soft tissue it can be used for region segmentation. Although much progress has been accomplished in automatic segmentation of medical ultrasound images, gynecological images received relatively less attention. As an example, automatic segmentation applied on the ovaries can only be rarely found in the literature [10–12, 17–19].

From the early days of medical imaging various thresholding approaches have been applied in order to segment medical images. Unlike in other imaging modalities, the gray levels in ultrasound images are not normally distributed. This fact makes the use of the well known Minimum Error Thresholding technique [20] inaccurate. Otsu's method [21], another widely used thresholding approach, is also inadequate in ultrasound since it provides a biased threshold when the gray level distribution functions have either unequal variances or populations.

Another important class of histogram-based thresholding algorithms are entropic methods. These techniques make use of the maximum entropy principle, originally discussed in information theory. The maximum entropy thresholding method proposed by Kapur et al. [22] is considered superior to other algorithms. However, there are cases in which Kapur's method performs poorly. For example, a significantly overestimated threshold is obtained for ultrasound images containing a dark lumen (transparent fluid) encircled by a bright region (tissue). Recently a new thresholding method, based on cross entropy, was suggested by Li and Lee [23]. This approach, known as "Minimum Cross Entropy Thresholding" (MCE), selects the threshold by minimizing the cross entropy between the original image and its segmented version. It was observed that usually MCE performs better than Kapur's algorithm in ultrasound images.

Brink and Pendock [24] proposed a thresholding technique which is a variation of the method presented by Li and Lee [23]. They considered two alternative definitions of the cross entropy (the one employed by Li and Lee and the one in which the roles of the original and the segmented images are reversed), and suggested to use either the latter one or their sum for thresholding. Using the sum introduces a symmetrical expression for the cross entropy.

Although two-dimensional (2D) extensions of entropic methods have been suggested [25, 26], they are generally time consuming and suffer partly from the drawbacks of the one-dimensional (1D) algorithms from which they were derived.

Herein a 2D extension of MCE, which uses a 1D summation is presented. Hence, it is almost as fast as the original 1D MCE algorithm. Generalizations to a more sophisticated 2D extension and to a multivariate algorithm are also discussed.

Combining the two components previously discussed—the local entropy and the 2D extension of MCE—a different scheme for segmentation of ultrasound images is presented herein. In this approach, the gray levels of the pixels and their local entropies form a 2D histogram. This 2D parameter space is reduced to a 1D histogram, while assigning equal weights to both variables. Then, MCE is applied on the obtained histogram. The above 2D MCE algorithm is tested on several ultrasound images and the results are compared to those obtained using only the gray level (conventional MCE) or the local entropy. It is demonstrated that 2D MCE is usually a better way to separate transparent fluid from soft tissue in ultrasound images.

The Local Entropy:

(a) Definition: A medical ultrasonic image usually shows various tissues. Suppose one deals with a region-of-interest (ROI) representing a single tissue. Let one select from the image a small window containing N pixels located within the tissue. The probability of having a pixel with gray level g in the window is:

$$P_g = \frac{N_g}{N} \qquad (1)$$

where $N_g$ is the number of pixels with gray level g in the tissue; and N is the total number of pixels in the window.

The local gray level entropy in the window can be defined as:

$$ENT = -\sum_{g=0}^{L} P_g \ln(P_g) \quad (2)$$

where L is the maximal possible gray level.

By definition, Pg describes the certainty that an arbitrary pixel has a gray level g. This certainty can be also measured by ln(Pg). Ignoring the negative sign, Equation (2) provides, in fact, the average value of ln(Pg) over all the possible values of g. Obviously, the average value of Pg (and hence, of ln(Pg) too) is expected to be larger for a homogeneous local region than for a heterogeneous one, since the former contains less gray values. The local entropy is therefore smaller for a homogeneous region.

The above discussion indicates that the local entropy measures the homogeneity of the local region. Since the local entropy evaluates the gray level spreading in the histogram, it is related to the variance in the window and can be considered as a textural feature of the tissue.

(b) Segmentation using the local entropy: In ultrasound images, the width of the local intensity histogram is correlated with its mean value. Such a correlation, which is related to the statistics of ultrasound speckle, has been previously demonstrated [27, 28]. As a consequence, a brighter region in the image exhibits a wider local gray level histogram and vice versa. The local entropy, which evaluates the width of the histogram, is therefore correlated with the local brightness.

It may seem odd to use the local entropy for region segmentation. This variable is considered much more suitable for boundary extraction, since near boundaries it usually occupies much higher values than inside regions; the large values of the local entropy near a boundary are caused by the variety of gray levels (related to both sides of the border) included in the window. In the comedical imaging, this description fits CT and MR images. In ultrasound images, unlike the former modalities, the local gray level histogram far from a boundary may spread over a range as wide as the histogram at the interface between two different tissues (each using the entire set of gray levels bounded by the histogram). Hence, the local entropies within and between tissues may be similar. This fact reduces the effectiveness and reliability of boundary extraction based on the entropy in ultrasound images.

Using the local entropy for region segmentation is possible because the local entropy is correlated with the local brightness. Generally, the quality of tissue discrimination is dependent on the contrast between the tissues. When an image contains regions representing water or another transparent fluid encircled by a soft tissue—regions representing fluid appear dark and demonstrate a narrow gray level distribution while regions representing soft tissue appear bright and have a much wider intensity distribution. In such cases, the local entropy of "fluid" is significantly smaller than the one of "soft tissue". Therefore, the local entropy can be used to differentiate between these two kinds of tissues in ultrasound images.

Minimum Cross Entropy Thresholding:

The notion of cross entropy was proposed by Kullback [29]. The cross entropy, which measures the information theoretic distance between two distributions P={P1, P2, ..., PN} and Q={q1, q2, ..., qN}, is expressed by:

$$D(Q, P) = \sum_{k=1}^{N} q_k \log_2\left(\frac{q_k}{p_k}\right) \quad (3)$$

Recently, Li and Lee [23] suggested a new thresholding method based on cross entropy, which is known as "Minimum Cross Entropy Thresholding" (MCE). In their method, the probability $q_k$ is formed by dividing the gray level of the $k^{th}$ pixel in the original image (assuming the image contains N pixels) to the sum of the gray levels in all the image pixels. Similarly, the probability $P_k$ is generated from the $k^{th}$ pixel in the segmented image (i.e., the binary image obtained after thresholding). These probability distributions are better understood if an image is viewed as an array of cells which is illuminated. The gray level at each cell then represents the number of photons reaching that cell. Hence, dividing each value by the total number of photons will provide the relative illumination at each cell. The above model, which provides an intuitive explanation for the choice of probability distributions, is discussed in [24].

The two gray levels that are used in the segmented image (one value for all the pixels below the threshold and the other value for the rest) can generally depend on the threshold. Li and Lee [23] used $\mu_1(t)$ and $\mu_2(t)$ (which are defined in Equation (4) below), as the gray levels of the pixels below and above the threshold t, respectively. Under this assumption, it can be shown that the cross entropy is proportional to the following expression [23]:

$$\eta(t) = \sum_{j=1}^{t-1} jh_j \ln\left(\frac{j}{\mu_1(t)}\right) + \sum_{j=t}^{L} jh_j \ln\left(\frac{j}{\mu_2(t)}\right) \text{ where} \quad (4)$$

$$\mu_1(t) = \frac{\sum_{j=0}^{t-1} jh_j}{\sum_{j=0}^{t-1} h_j} \text{ and } \mu_2(t) = \frac{\sum_{j=t}^{L} jh_j}{\sum_{j=t}^{L} h_j}$$

wherein, $h_j$=the number of pixels having gray level j.

Obviously, minimizing η(t) is equivalent to minimizing the cross entropy between the original image and its segmented version. Hence, the optimal threshold is the value of t which minimizes η(t).

Two-dimensional MCE:

It was previously shown that the thresholding criterion in MCE is given by:

$$\eta(t) = \sum_{j<t} jh_j \ln\left(\frac{j}{\mu_1(t)}\right) + \sum_{j\geq t} jh_j \ln\left(\frac{j}{\mu_2(t)}\right) \quad (5)$$

This expression will now be generalized to a 2D parameter space while maintaining the 1D summation. A possible form of such generalized Equation may be:

$$\eta(t) = \sum_{K(i,j)<t} K(i,j) h_{K(i,j)} \ln\left(\frac{K(i,j)}{\mu_1(t)}\right) + \sum_{K(i,j)\geq t} K(i,j) h_{K(i,j)} \ln\left(\frac{K(i,j)}{\mu_2(t)}\right) \quad (6)$$

K(i,j) is symmetric with respect to i,j and reduces to the 1D expression when only one variable is considered.

Since the formal values of i and j affect the value of K, one assumes, for simplicity, that both variables occupy the same range of possible values.

In order to find good candidates for K(i,j) the problem is herein analyzed from a geometrical point of view. One knows that Equation (5) describes a sum over a 1D vector. In fact, each element in the sum is associated with a cell whose distance from the origin is j. The obvious generalization to two dimensions should involve an elementary "cell" in the 2D matrix whose distance from the origin (i.e. radius) is K(i,j). Two candidates for K(i,j), which have simple geometrical meaning, can be suggested:

$$K_1(i,j) = i+j \quad (7)$$

$$K_2(i,j) = \sqrt{i^2 + 30j^2} \quad (8)$$

In the first case, the sum is computed on straight lines obeying i+j=C, while in the second case the sum is computed on circular rings obeying $\sqrt{i^2+j^2}$=C.

FIG. 1 demonstrates how the computation is performed in both cases. In each part of the Figure, the filled area represents the part of the parameter space in which K(i,j) <C (for a specific value of C) while the empty area shows the rest of the matrix. The curve shows the matrix elements for which the distance from the origin is C.

Let one now consider the function K(i,j) as a new variable k, and construct its histogram. Each cell in this histogram will contain a contribution only from a unique line or ring (depending on the case) in the 2D matrix. Hence, the 2D parameter space was reduced to a 1D histogram of the variable k. Using Equation (6), it can be seen that the thresholding criterion for k is given by:

$$\eta(t) = \sum_{k<t} kh_k \ln\left(\frac{k}{\mu_1(t)}\right) + \sum_{k\geq t} kh_k \ln\left(\frac{k}{\mu_2(t)}\right) \text{ where} \quad (9)$$

$$\mu_1(t) = \frac{\sum_{k<t} kh_k}{\sum_{k<t} h_k} \text{ and } \mu_2(t) = \frac{\sum_{k\geq t} kh_k}{\sum_{k\geq t} h_k}$$

One sees that the regular 1D criterion for MCE is obtained. Hence, one can apply regular MCE on the histogram of k and find a threshold. If the curve in FIG. 1 signifies K(i,j)=t (where t is the obtained threshold), the pixels in the filled region would be below the threshold while the rest would be above it.

The entire process can be viewed as clustering. Since the pixels from each tissue form a cluster in the parameter space, the curve K(i,j)=t can be viewed as a decision curve separating the clusters. Clustering is performed using the cross entropy as a metric, and η(t) as the expression to be minimized.

Generalizations:

(a) Generalization to unequal weights: So far, K(i,j) was limited to functions symmetric with respect to i and j. However, this special case can be generalized to functions of the form:

$$K_1(i,j) = a \cdot i + b \cdot j \quad (10)$$

$$K_2(i,j) = \sqrt{a^2 i^2 + 30 b^2 j^2} \quad (11)$$

These Equations, in which each variable is preceded by a coefficient, can be viewed as combinations of i and j with non-equal weights.

Equations (7) and (8) represent the special case in which equal weights are used. By selecting the coefficients, the user can determine the relative importance of each variable in the thresholding process.

It is desired to keep the values of K(i,j) in the range of i's and j's, so that t does not become multiplied by an arbitrary factor. Hence, the expression for K(i,j) must be normalized. The new coefficients should be defined as true weights (i.e. their sum must be 1). Hence, the normalized version of Equations (10) and (11), respectively, will be:

$$K_1(i,j) = w_1 i + w_2 j \quad (12)$$

$$\text{where: } w_1 = \frac{a}{a+b}, \quad w_2 = 1 - w_1 = \frac{b}{a+b}$$

$$K_2(i,j) = \sqrt{w_1^2 i^2 + w_2^2 j^2} \quad (13)$$

$$\text{where: } w_1^2 = \frac{a^2}{a^2+b^2}, \quad w_2^2 = 1 - w_1^2 = \frac{b^2}{a^2+b^2}$$

It should be noticed that in order for Equations (12), (13) to be reduced to Equations (7), (8) respectively, when equal weights are used, Equation (12) should be multiplied by 2 and Equation (13) should be multiplied by √2.

From a geometrical point of view, Equation (12) means summing on straight lines with a general slope (instead of lines with slope −1) and Equation (13) means summing on elliptical rings (instead of circular rings). It follows that the decision curve between the two clusters in the parameter space is either a line with a pre-determined slope or an elliptical arc. Any knowledge about the shapes of the two clusters may be used to optimize the weights, in order to obtain a better decision curve.

(b) Generalization to multivariate threshold: Until now, the discussion was restricted to bivariate thresholding. However, it may be desired to consider several different variables for segmentation. The modification of Equations (12) and (13), respectively, for multivariate thresholding is:

$$K_1(x_1, x_2, \ldots, x_N) = \sum_{i=1}^{N} w_i x_i \quad (14)$$

$$\text{where: } \sum_{i=1}^{N} w_i = 1$$

$$K_2(x_1, x_2, \ldots, x_N) = \sqrt{\sum_{i=1}^{N} w_i^2 x_i^2} \quad (15)$$

$$\text{where: } \sum_{i=1}^{N} w_i^2 = 1$$

In this case the decision curve is replaced by a decision surface. This surface can be either a plane or an ellipsoid.

(c) Generalization to other thresholding methods: This Example discusses a 2D extension of MCE. In principle, the same idea can be applied to other thresholding techniques. A general scheme for thresholding would be:

1. Construct K(x$_1$,x$_2$, . . . , x$_N$) using the selected set of variables and coefficients.
2. Sort the pixels in the image according to their k value.
3. Find the threshold for k using the desired thresholding method.
4. Segment the image.

Combining the Local Entropy with 2D MCE:

Multivariate MCE can be applied using any set of variables. It was chosen to focus on the 2D case, where the pair of variables are the gray level and the local entropy. The motivation for using the local entropy was its relative robustness to gray level variations. Both straight and elliptic decision curves (Equations (12) and (13), respectively) have been tested, but the simpler selection (straight line) was found to be sufficient. Thus, implementing 2D MCE where the variable K(i,j) is determined by a linear combination of the gray level and the local entropy was attempted.

Segmentation Results:

Using Equation (12) a 2D MCE was applied on several ultrasound images containing ovarian cysts (fluid) encircled by ovarian tissue (soft tissue). Various weights were tried for the intensity and local entropy, and it was discovered that when the fluid does not contain significant noise—equal weights are sufficient. It was also evident that the original method proposed by Li and Lee [23] frequently failed to segment these images satisfactorily. The results obtained were compared for equal weights to those formed when zero weight was given either to the gray level or to the local entropy. The later case (zero weight to the local entropy) is easily identified as the conventional MCE technique.

The images presented herein were obtained using the Aloka SSD-680 scanner (Aloka, Tokyo, Japan) with a 5 MHz transvaginal probe with 128 channels. The images were recorded on video cassettes, and later digitized into the computer.

For each image a ROI was selected, which contained only the two relevant tissues, and performed all computations on this ROI. Various sizes of windows were tested for computing the local entropy of each pixel, and it was discovered that good results are obtained in the range 7×7 to 15×15 pixels. Hence, in this study a window size of 11×11 pixels was selected and such are the results hereby presented.

Figure 2:
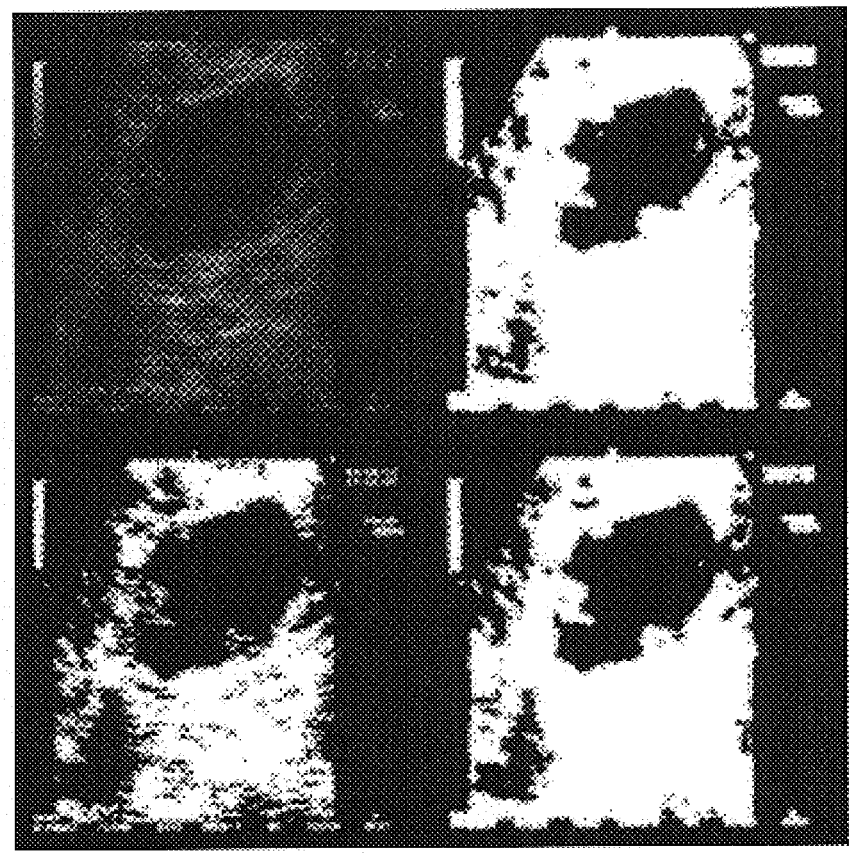
FIG. 2 show segmentation results for an ovarian cyst with transparent fluid (example 1). Top left—original image; top right—segmentation using the local entropy; bottom left—segmentation using the gray level (conventional MCE); bottom right—segmentation using both variables (2D MCE).
Figure 3:
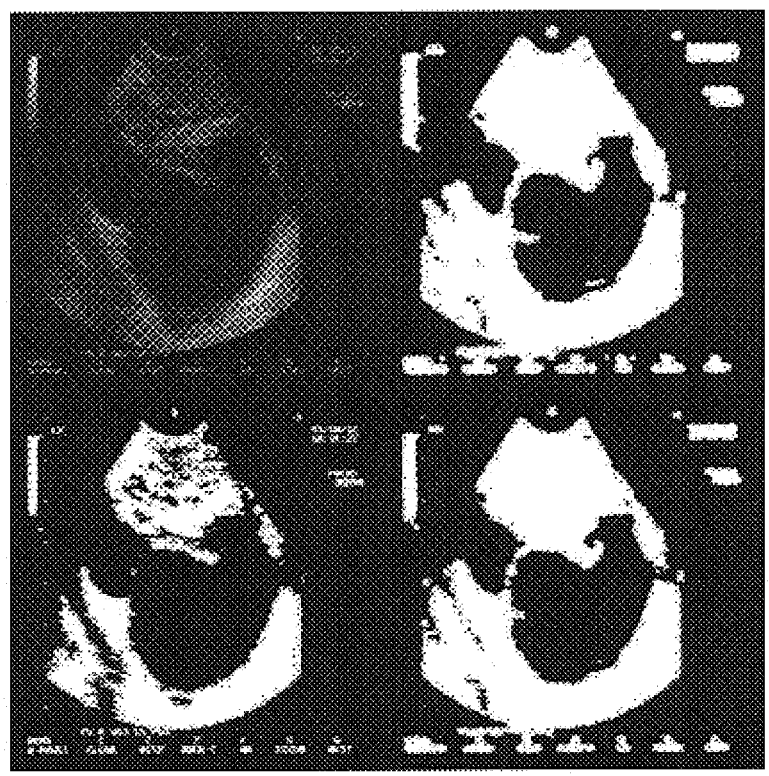
FIG. 3 shows segmentation results for an ovarian cyst with transparent fluid (example 2). Top left—original image; top right—segmentation using the local entropy; bottom left—segmentation using the gray level (conventional MCE); bottom right—segmentation using both variables (2D MCE).
Figure 4:
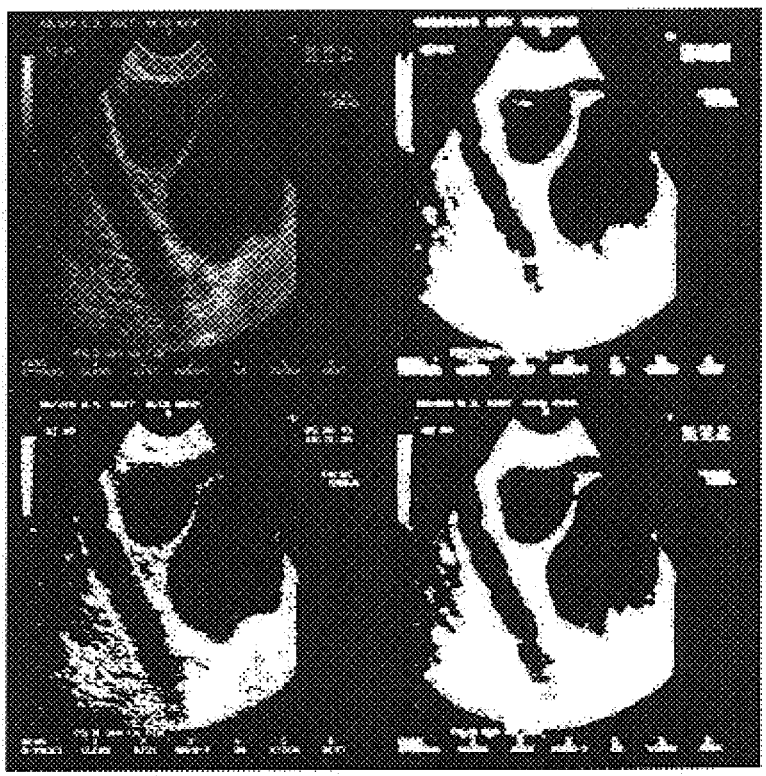
FIG. 4 shows segmentation results for an ovarian cyst with transparent fluid (example 3). Top left—original image; top right—segmentation using the local entropy; bottom left—segmentation using the gray level (conventional MCE); bottom right—segmentation using both variables (2D MCE).

FIGS. 2–4 provide examples of the results obtained when the tested images are composed of transparent fluid (dark fluid without bright noise) and soft tissue. Each figure contains 4 images: top left—the original image, top right—the segmented image formed considering only the local entropy, bottom left—the segmented image generated considering only the gray level (conventional MCE), bottom right—the segmented image obtained using equal weights (2D MCE).

It can be concluded from these Figures that conventional MCE sometimes yields reasonable results (e.g., FIG. 4), but in many occasions the threshold is significantly overestimated (e.g., FIGS. 2–3). Hence, frequently much of the soft tissue in the image (including locations where fine details are important) is misclassified as fluid.

Thresholding the local entropy, on the contrary, provides overestimated bright regions. This is because windows selected near the boundary take into account pixels from both tissues, and also since the fluid near the boundary frequently contains regions of brighter pixels. Both options, which result in a wide local intensity histogram, relate the boundary to large values of the local entropy. Hence, parts of the boundary region are misclassified as bright tissue.

The 2D MCE algorithm used herein seems to provide the best results in most cases. A clear example is FIG. 3, where fine details of the fluid-tissue boundary are lost both in the bottom-left and the top-right images. The images obtained using 2D MCE show a small degree of overestimation in the soft tissue. The effect can be reduced by peeling off several layers of bright pixels near the boundaries. This can be easily performed, for example, using morphological operators such as erosion. Further investigation is obviously required in order to enable a quantitative use of the obtained results. In those cases where conventional MCE seems to be equal or superior to 2D MCE (e.g., FIG. 4), it is worthwhile to observe that the segmented image after 1D MCE "preserves" the textural properties of the image (i.e., the white regions are full of discontinuities in a pattern similar to the original texture). The binary image obtained from 2D MCE, on the contrary, demonstrates much more homogeneous bright regions. When further image processing steps (e.g., boundary extraction or shape classification) rather than a simple display are to follow segmentation, as further detailed hereinunder, the result obtained from using 2D MCE might be considered better.

Figure 5:
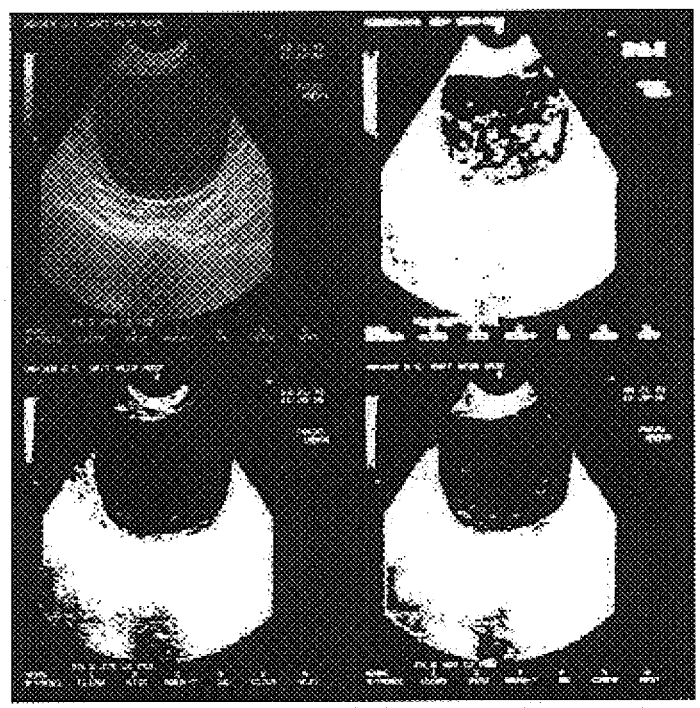
FIG. 5 shows segmentation results for an ovarian cyst with turbid fluid (example 4). Top left—original image; top right—segmentation using the local entropy; bottom left—segmentation using the gray level (conventional MCE); bottom right—segmentation using both variables (2D MCE).
Figure 6A:
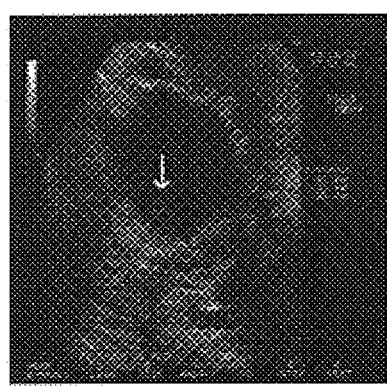
FIGS. 6a–d show examples of various structures within a cyst.
Figure 6B:
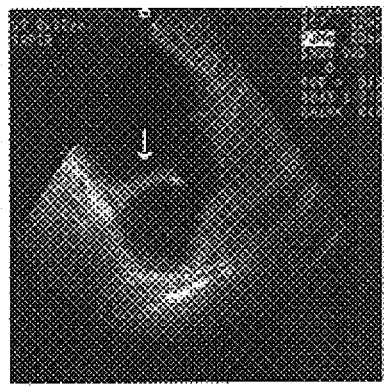
Figure 6C:
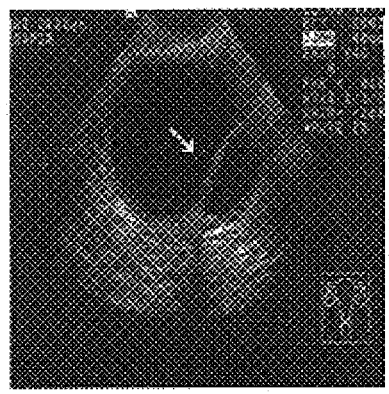
Figure 6D:
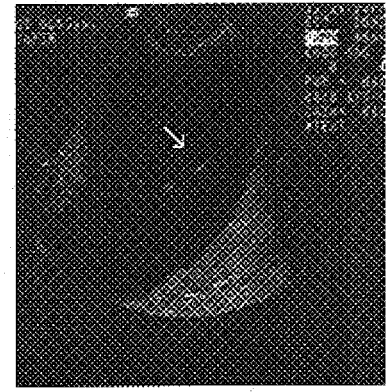

Although the 2D MCE algorithm was primarily designed for completely dark fluid, it was tested also on cysts containing fluid full of small scatterers (bright spots). FIG. 5 demonstrates the results obtained for turbid fluid. It was found that for cysts containing dark fluid with bright spots conventional MCE (which is equivalent to 2D MCE with zero weight to the local entropy) is optimal.

It is generally expected that 2D MCE will have only limited use for images which demonstrate low contrast between the different tissues (e.g., solid ovarian masses), because in such images the local entropy distributions of the various tissues partially or completely overlap. However, when the ovarian mass contains cystic areas although it is predominately solid—applying 2D MCE may still be advantageous for specific tasks. Other region or boundary extracting algorithms can be used in such cases.

The 2D extension were also tested employing the formulas presented by Brink and Pendock [24]. It was found that the obtained results were almost identical to those based on the expression provided by Li and Lee [23]. Both algorithms are therefore equivalent.

In order to quantitatively assess the performance of the 2D MCE method, the obtained results (using 2D MCE with equal weights) were compared with those of an experienced observer. The observer was unaware of the results provided by the automatic algorithm, seeing only the original ultrasound images (before segmentation). After short training (on an image not involved in the comparison), the observer manually outlined the boundaries of the cysts presented in FIGS. 2–5. In case the cyst expanded beyond the sector, the boundary of the sector was traced. The region representing each cyst was then obtained by filling the cavity encircled by each outlined boundary.

Using the obtained images, the size (i.e., area) of each cyst resulted from manual tracing was compared to the size provided by automatic segmentation. It was found that the manually obtained cyst was always slightly larger than the automatically generated one; for all four cases (FIGS. 2–5) the observed underestimation was in the range 5–7% (taking the manual result as 100%). The difference can be visually interpreted as a 2-to-3-pixel-thick boundary layer. These quantitative results are encouraging, especially when computing the volume of the cyst (using a series of images) is set as the ultimate goal.

The above results, demonstrated in FIGS. 2–5, indicate that MCE (including its conventional and 2D versions) segments the images reasonably well. Bivariate (i.e., 2D) MCE is preferred when uniform regions and fine (or faint) details are extremely important; conventional MCE is selected when small bright spots are not desired (turbid fluid) or when one wishes to preserve the "natural" texture of the image. Applying 2D MCE with unequal weights may provide a general solution to a wide variety of image properties and user requirements.

Thus, in this Example, a multi-dimensional extension of Minimum Cross Entropy thresholding (MCE) has been presented. The new version replaces the segmented variable (gray level) by a weighted combination of several image parameters. It is proposed to use a 2D extension of MCE, which employs a linear combination of the gray level and the local entropy, in order to segment ultrasound images containing fluid surrounded by a soft tissue. The algorithm was tested on ultrasound images of ovarian cysts. For cysts containing transparent fluid, bivariate MCE usually segmented the images better than univariate (conventional) MCE.

Example 2

Computerized Quantification of Structures within Ovarian Cysts Using Ultrasound Images Ovarian cysts are a common type of ovarian mass. The morphology of cysts, as it appears in ultrasound images, is currently used for classification of ovarian pathologies. However, this classification process is based on human interpretation of the sonographic image. In this Example, a semi-automatic algorithm for the quantification of ovarian cysts is presented. This algorithm categorizes the structures within a cyst and extracts their quantitative geometrical properties (e.g., width, characteristic diameter). In order to assess the validity of the technique, its performance was compared to human classification and manual measurements made by an expert. The results show a good match between automatic evaluations made by a computer and those of an experienced observer, indicating a potential for clinical use.

As already mentioned, ovarian cysts are the most common type of ovarian mass observed in the clinical setting. Being filled with fluid within the ovary, they usually appear in B-Scan ultrasound images as relatively dark (hypo echogenic) regions surrounded by bright tissue. An ovarian cyst can be characterized by its size, the nature and appearance of the fluid, the thickness and regularity of its boundaries, and the existence and properties of various structures therewithin. The link between the morphology of the cyst and its potential malignancy has led to the use of these properties, as well as others, in the differential diagnosis of ovarian cysts. A quantitative analysis of these morphological properties is performed, in order to assess the malignancy of the ovarian pathology, using scoring systems [2–6]. The idea is to score several properties of the ovarian mass, according to a pre-determined table, and to use the resulting value (the sum of the individual scores) for classification. However, the scoring process is based on human visual evaluations by an experienced observer which do not exploit the advantages of computerized analysis.

In this Example, an algorithm for the quantification of ovarian cysts is presented. The method exemplified refers primarily to structures within the cyst (e.g., papillations, septations), categorizing them and extracting quantitative data about their properties.

In order to assess the validity of the technique, the performance of the presented algorithm was compared to evaluations made by an expert gynecologist. A statistical analysis of the results determines the performance of the algorithm. It will be appreciated that there were no previous attempts to automatically extract morphological features from ultrasound images of ovarian cysts.

The Morphology of Cysts in Ultrasound Images:

An ovarian cyst appears in an ultrasound image as a relatively dark region, whereas the surrounding solid tissue appears brighter (see FIGS. 6a–d). The cyst may be either unilocular (i.e., composed of a single lumen) or multilocular (i.e., separated into several parts). In the latter case, each part can be treated as a separate cyst.

A cyst can generally contain two major types of morphological structures: papillations and septations. A papillation is a small region of 15 ovarian tissue penetrating from the boundary of the cyst into its lumen. A septation is a narrow strip of ovarian tissue which penetrates the lumen and divides the volume into several segments. An important difference between papillations and septations is that septations are generally much more elongated than papillations. Examples of various structures found within an ovarian cyst are shown in FIGS. 6a–d.

A septation can be classified either as complete or incomplete. When a septation is complete, several separated cystic lumens are generated (hence forming a multilocular cyst). For an incomplete septation, the cystic region remains unilocular. A complete septation may also look incomplete in the image due to poor contrast. Furthermore, poor imaging parameters or improper viewing angle may diminish the edges of a septation, hence causing it to appear as a strip located inside the cyst. A similar effect can also be observed for papillary structures. Finally, when multi-septated (multilocular) cysts are analyzed, a value describing the maximal thickness possible for a (complete) septation should be pre-determined. Cystic lumens separated by a wider strip of tissue can be considered uncorrelated. The existence, the number, and the dimensions of these structures are important indicators for the potential malignancy of the cyst. It should be emphasized that the partition into complete and incomplete structures is not a common definition in medical sonographic diagnosis; it is however adopted herein clearly in order to describe the algorithm.

Figure 7:
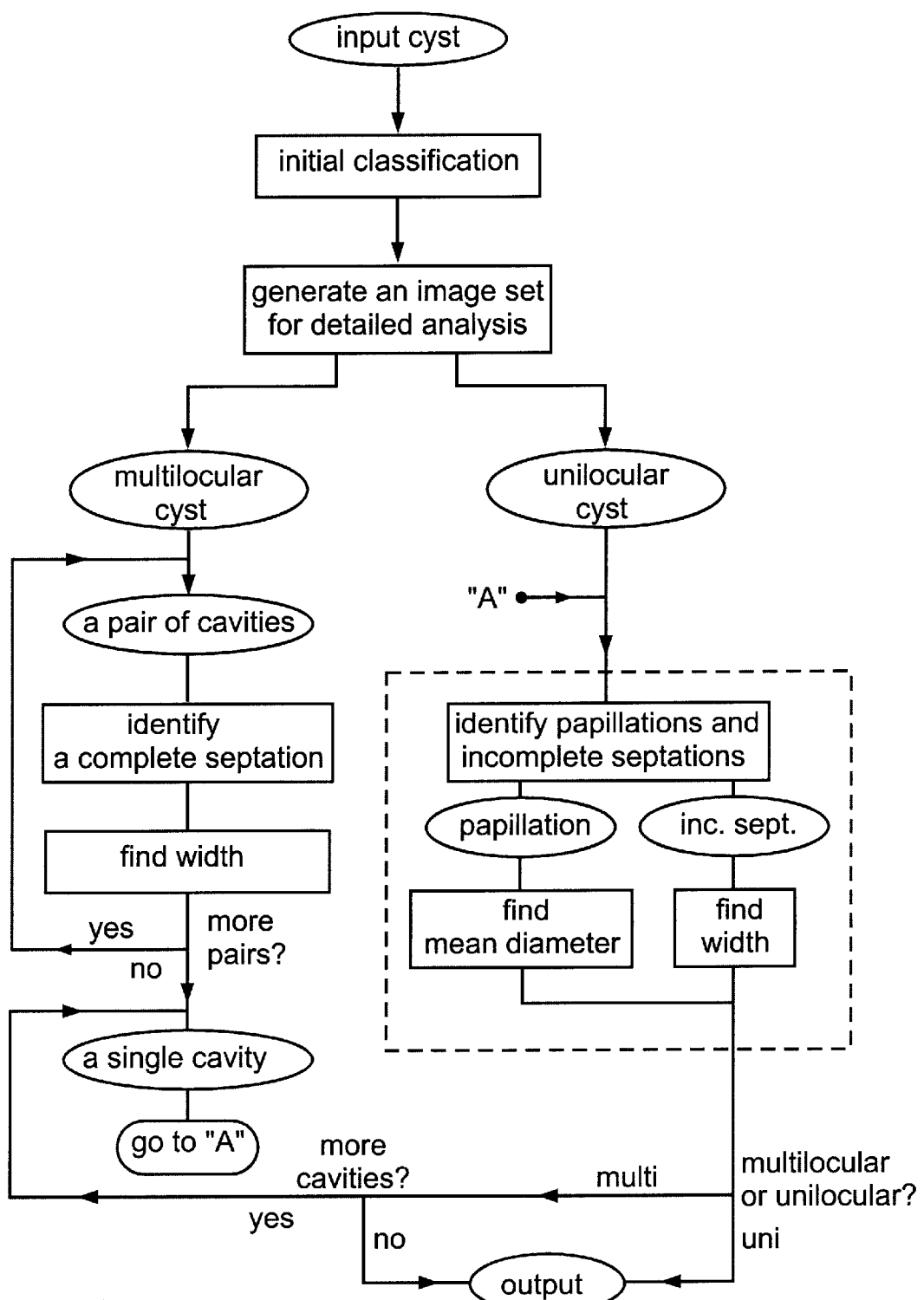
FIG. 7 is a flow chart describing the main steps of an algorithm according to the present invention used for automatic classification and quantitative evaluation of adnexal masses, wherein an ellipse represents data and a rectangle represents an operation.

The Algorithm—An Overview:

The algorithm developed in accordance with the gist of the present invention identifies the various structures within a cyst, categorizes them, and quantitatively characterizes their geometry. From this analysis, the number, location, and dimensions of the various structures within each cyst are extracted. A flow chart describing the main steps of the algorithm is provided in FIG. 7. In FIG. 7, data (usually an image) are represented by an ellipse and an operation (a task) is represented by a rectangle.

As illustrated in FIG. 7, the method first separates multilocular cysts from unilocular ones. In case of multi-septated cysts, the algorithm first analyzes pairs of cystic cavities in order to evaluate the widths of the separating complete septations. Only then, is each cystic region addressed separately, the structures (e.g., papillations, incomplete septations) are identified and analyzed. If the original cyst is unilocular, only the latter part of the analysis is performed, as shown in FIG. 7.

The analysis of papillations and incomplete septations within a single cystic cavity (whether an original unilocular cyst or part of a multi-septated cyst) is basically divided into classification (which includes identifying both structure types and ruling out false structures) and quantitative computations. Classification (to papillations, incomplete septations, etc.) is performed using several geometrical properties of the ovarian structures and the minimum error rate Bayes classifier [16]. Then, the characteristic dimensions of each structure (the mean diameter of each papillation, the width of each septation) are assessed using mathematical morphology (see is Example 4). Both parts (identification and measurements) are described in FIG. 7.

Preliminary Steps:

Preliminary classification: The initial step in analyzing the cyst is sorting it into one of two categories: unilocular or multilocular. The images used are such in which the cysts ("objects") are represented by a specific gray level while the rest of the image ("background") is represented by another gray level. The required initial classification can then be easily performed by counting the number of unconnected cystic regions in the image.

The following detailed analysis is performed on images containing either a single cyst (for most structures) or two cystic parts (for analyzing a complete septation). This set of images is therefore constructed prior to structure analysis (see second rectangle from top in FIG. 7). As part of this preliminary step, the obtained images are further processed so that each cystic structure is separately indicated. The mathematical technique used is described in detail in the following sub-section.

Isolating the various cystic structures: Structure separation begins by computing the convex hull of the cyst, which is the smallest polygon circumscribing the cyst (see FIGS. 8a–b). Example 3 below provides a mathematical background about the convex hull, and presents a simple method for computing it. Subtracting the original object from its convex hull provides the convex deficiency of the cyst. The convex deficiency of the cyst is composed of several separated regions, each associated with a single cystic structure (e.g., the gray regions in FIG. 8a). This description is also valid for images containing two cystic regions (see FIG. 8b).

The regions composing the convex deficiency may often overestimate the corresponding cystic structures (e.g., the outer parts of the septations in FIGS. 8a–b. On other occasions, two small cystic structures may connect. Consequently, the convex deficiency of the cyst is used as an upper limit for the area representing cystic structures (i.e., structures within a cyst or between two cystic regions).

Then, a new image is formed by applying morphological closing with a binary disc (a roundly shaped structuring element) on the original object (the cyst itself). A detailed discussion on mathematical morphology in general and morphological closing with a disc in particular is provided in Example 4 hereinunder. The obtained image exhibits partial filling of the concavities in the cyst (which correspond to cystic structures), leaving a crater in the outer part of the concavity (see FIG. 9b). Since closing with a disc of radius r fills only cavities wider than r, a smaller disc results in less filling and a deeper crater. The radius of the applied disc for each cystic structure was determined as the minimal radius (from the series r=20, 30 and 40 pixels) which fills more than 50% of the corresponding part of the convex deficiency. When all three discs filled a smaller portion of the region (probably leading to underestimation of the cystic structure), the convex deficiency and not the result of morphological closing was used for describing that cystic structure.

As can be seen from FIGS. 9a–b, the craters formed by morphological closing cause a small underestimation of the corresponded structures. To eliminate this artifact, each region that was added to the cyst by morphological closing (if a single region in the original convex deficiency was broken into several separate sub-regions, we address each one of them separately) was replaces by its convex hull (computed as explained in Example 3 hereinbelow). The results obtained are displayed in FIG. 9c.

The images used in the rest of the algorithm according to the present invention are those obtained after the steps above, an example in Given in FIG. 9c. In these images, the area added to the cyst can be viewed as a corrected convex deficiency. This area is henceforth referred to as the convex deficiency (rather than using the term for the region associated with the actual convex hull).

Analyzing Complete Septations:

The analysis of a complete septation is performed on an image containing two "objects" (cysts) surrounded by "background", after computing (as described above) the corrected convex hull and convex deficiency (FIG. 9c is an example). The only part of the convex deficiency which is connected to both cysts is found and isolated, since it contains the analyzed septation. Furthermore, its boundary segment which is connected to one of the objects (this segment is henceforth called "edge 1"), and the segment connected to the other object (henceforth called "edge 2") are also identified.

The septation between the two cysts can be visually described by a straight line passing from a point on edge 1 to a point on edge 2. Since the distance between the two opposite edges varies significantly, the problem is to find a pair of edge points, yielding a "correct" septation (i.e., whose width agrees with manual evaluation). It should be noted that one seeks the length of the line (width of septation) rather than its exact location.

In order to save computation time, the shorter segment among edge 1 and edge 2 is first selected. Then, for every point on the selected edge, the shortest line connecting this point and a point on the other edge is found. The obtained set of minimal distances are preserved as candidates for the width of the septation.

Contrary to intuition, the mean (or even the median) distance cannot be used as a reliable assessment of the septation width, because of the large values contributed by lines located where edge 1 is far from edge 2. However, this contribution is spread over a relatively large range of values, whereas many lines are characterized by values close to the correct width (otherwise this width is meaningless). Consequently, a histogram of the computed distances is generated, followed by rounding each value to the nearest 0.5 pixel (using a 0.5 pixel precision is sufficient for the purpose described). Then, the most frequent value (i.e., the maximal peak) in the histogram is expected to represent the correct septation width. In order to avoid various artifacts, this histogram was smoothed before peak detection using a conventional three-cell Gaussian filter. In other words, each cell in the histogram was weighted with its two nearest neighbors using the formula:

$$h(k)=0.25 \cdot h_0(k-1)+0.5 \cdot h_0(k)+0.25 \cdot h_0(k+1) \qquad (16)$$

where, $h_0(k)$ is the $k^{th}$ cell in the original histogram and $h(k)$ is the $k^{th}$ cell in the filtered histogram.

Finally, peak detection is applied on the filtered histogram and the global peak is taken as the evaluated width of the complete septation. In case the obtained width is larger than a pre-defined value (the structure is too thick to be considered a septation), the result is rejected. When several complete septations are found in the same image, the above procedure is repeated for every septation (i.e., every pair of separated cysts).

Analyzing Papillations and Incomplete Septations:

The initial image: The analysis described below is preceded by computing the corrected convex hull and convex deficiency of an image containing only the selected cyst ("object") surrounded by "background". Excluding rare cases, each part of the convex deficiency includes either a single structure or none. Generally, a specific part of the convex deficiency can represent a papillation, an incomplete septation, or a region which is irrelevant to the medical diagnosis (henceforth called "side") and appears as a result of local concavities in the boundary of the cyst.

When the original image (the B-scan) is faint or suffers from poor contrast, the region linking the structure to the surrounding tissue may disappear and the structure may appear as located entirely inside the cyst. The scanning angle can also induce a similar effect. Luckily, these regions are also included (as separate parts) in the convex deficiency, and can thus be geometrically analyzed. Again, such a region can contain a papillation (henceforth called "internal papillation"), a septation (henceforth called "internal septation"), or a meaningless structure generated due to small bright noises within the cyst.

Feature selection: A variety of geometrical parameters can be used for shape analysis. Three relatively simple variables were chosen as shape features herein. Two of them are the area and roundness of the shape. The third variable provides the relative part of its boundary touching the cyst.

The area of the inspected region, easily obtained by pixel counting, is used to eliminate small deficiency parts. Since the convex deficiency of a cyst usually contains a large number of small "sides" (regions formed near local boundary concavities), a preliminary step eliminating these false structures saves much of the computation time and simplifies the rest of the classification algorithm. The same principle applies for cases in which the false structure is entirely located within the cyst. The criterion used for rejecting false structures was an area smaller than 1% of the area of the cyst.

The compactness (also called "roundness") of a shape [30] is a measure that assesses to what extent a shape is elongated. The reason for using this feature is that septations are generally elongated whereas papillations are not.

The compactness of a shape is given by:

$$\text{comp} = \frac{(\text{perimeter})^2}{4\pi \cdot \text{area}} \quad (17)$$

The compactness is minimized for a disc, for which it equals 1.

The last variable used we call "pop". This parameter provides the relative part of the shape's perimeter (in percent) connected to the cyst, and is formally defined as:

$$\text{pop} = 100 \times \frac{\text{length of portion touching cyst}}{\text{total length of perimeter}} \quad (18)$$

This geometrical feature is selected because different types of structures are related to significantly different "pop" values. For an incomplete septation, most of the boundary (typically 75–95%) touches the object (the cyst) and only a relatively small fraction is connected to the background. For a papillation, a smaller part of the boundary (typically 60–80%) is connected to the cyst. Finally, only about half the perimeter (usually 50–60%) touches the cyst for a "side". When "internal" structures are involved, "pop" obviously equals 100 since the entire structure is surrounded by the cyst.

Although each variable provides means for classification, a single parameter generally cannot be used alone due to an overlay between the values obtained for different types of structures. Hence, a multivariate analysis is required. The details of the selected technique are discussed below.

Classifying the structures: After eliminating small false structures, two basic situations must be addressed: shapes representing structures touching the cyst and shapes related to "internal" structures. The latter case can be easily identified by checking whether the "pop" of the shape equals 100 (or very close to it, to avoid artifacts).

When the analyzed shape is connected to the cyst, a bivariate analysis is performed in a two-dimensional feature space containing the compactness of the shape and the relative part of its boundary touching the cyst. The well known minimum error rate Bayes classifier [16] was chosen, assuming that each class (papillation, incomplete septation, side) is bivariate normal. The mathematical principles of minimum error rate classification are provided in Example 5 hereinunder.

The available data about a specific shape is described as a feature vector x in a two-dimensional feature space. Then, this shape belongs to class j which yields a minimal value of the following expression $$F_k = (x - \mu_k)^t {}_k^{-1}(x - \mu_k) + 1n(|\Sigma_k|) \quad (19)$$

where k is 1, 2, 3; $\mu_k$ is the mean vector for class k; and $\Sigma_k$=the covariance matrix for class k.

In order to apply the technique, the mean vectors and the covariance matrices characterizing the three classes must be known. Hence, first these variables were computed using a training sample set (which included only cases for which the structure type was evident). Then, the classification technique was applied on a test group of unidentified shapes using the obtained values.

When the analyzed shape is fully contained in the cyst ("internal" structures), a univariate analysis was performed based on the compactness of the structure. For this analysis no training is required. Instead, the means and variances of the Gaussians are taken from the data computed for papillations and incomplete septations. Sides are not considered since it is assumed that all "internal" false structures were previously eliminated based on their small size. Then, the "internal" structures are sorted using one-dimensional minimum error rate classification.

Quantitative analysis: The method used to extract the quantitative data from the identified structures is based on morphological erosions (see Example 4) with various structuring elements. In this technique, the characteristic dimension of the examined object (namely, width or characteristic diameter) is assessed as twice the number of successive erosions (with the same structuring element) required to eliminate the entire object.

Figure 10A:
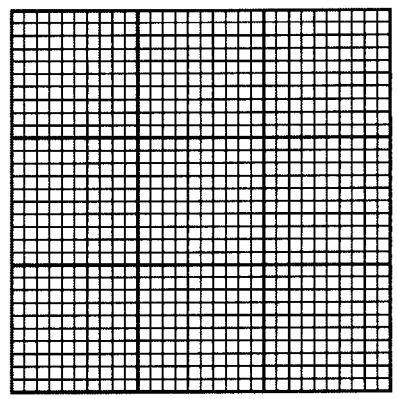
FIGS. 10a–e demonstrate the structuring elements used for morphological erosions during quantitative analysis with the algorithm is according to the present invention.
Figure 10B:
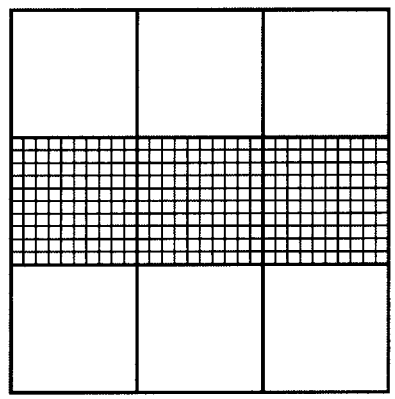
Figure 10C:
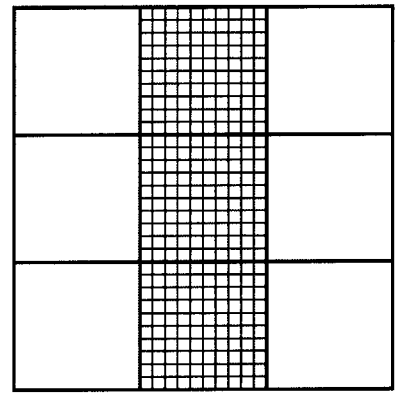
Figure 10D:
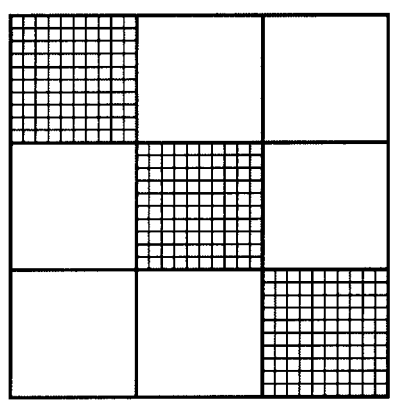
Figure 10E:
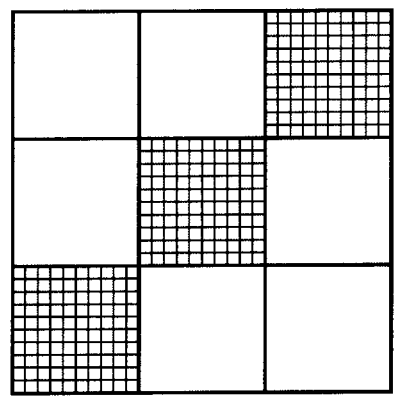

For a septation (incomplete or "internal"), the structure was eroded with a 3×3 square (FIG. 10a), and the obtained value was used as the evaluated septation width. Since successive erosions with a square evaluate the short axis (i.e., actual thickness) of the object, using a square is suitable for elongated objects such as septations. Papillations, however, are not elongated and hence better represented by their mean diameter For a papillation (including "internal" ones), the structure was eroded with four different three-pixel-long structuring elements, each centered at the examined pixel: a horizontal line (FIG. 10b), a vertical line (FIG. 10c), and two diagonal segments (FIGS. 10d–e). For each structuring element, the number of erosions required to erase the object was found, hence providing evaluations of its thickness along four different axes. Then, the median of these four values (computed by excluding the two extreme results and finding the average of the two remaining ones) was computed and used as the evaluated mean diameter of the papillation.

Image Acquisition:

In this Example, a B-scan transvaginal sonographic images were employed. These images were partly obtained using the Acuson 128XP/10 scanner (Acuson, Mountain View, Calif., USA) with a 5–7 MHz transvaginal probe. The rest were generated by the Aloka SSD-680 (Aloka, Tokyo, Japan) with a 5 MHz transvaginal probe. All the images were recorded on video cassettes (VHS format), and later digitized into the computer using a DT-2853 frame grabber (Data Translation, Marlboro, Mass., USA), yielding images containing 512 pixels×512 pixels×256 gray levels. The algorithm was developed on a Silicon Graphics workstation, using version 4.2c of Matlab for multivariate analysis.

Results:

The initial data base: The algorithm described herein was tested on 99 ultrasound images displaying ovarian cysts with a variety of morphological appearances. Each cyst contained from none to several morphological structures. The boundaries of each cyst were manually traced by an expert physician (RT), who also identified (and classified) each structure and (for most structures) manually evaluated its characteristic parameters (diameter of papillation, width of septation). From these boundaries, images isolating each cyst structure (as a separate part of the corrected convex deficiency) were generated.

A basic assumption in the performance evaluation process was that each structure could be definitively classified by the expert. In fact, the expert was required to classify a small number of structures that he considered borderline cases. Such ambiguous structures exhibit geometrical characteristics of two different structure types (usually, a papillation and a septation). When the structure actually has borderline characteristics, its categorization is meaningless. When this ambiguity is caused by a poor viewing angle, the ultrasonographer can simply select a better angle and use the obtained image (rejecting the ambiguous one) for automatic analysis. It is therefore believe that the performances of the algorithm for cysts with borderline structures should be a minor consideration in the evaluation process.

As a result, structures which the expert defined as ambiguous (two papillations and four incomplete septations) were excluded from the obtained data set the. It should be emphasized that only true borderline cases were excluded, leaving structures with various degrees of similarity to "classical" papillations and septations.

Figure 11:
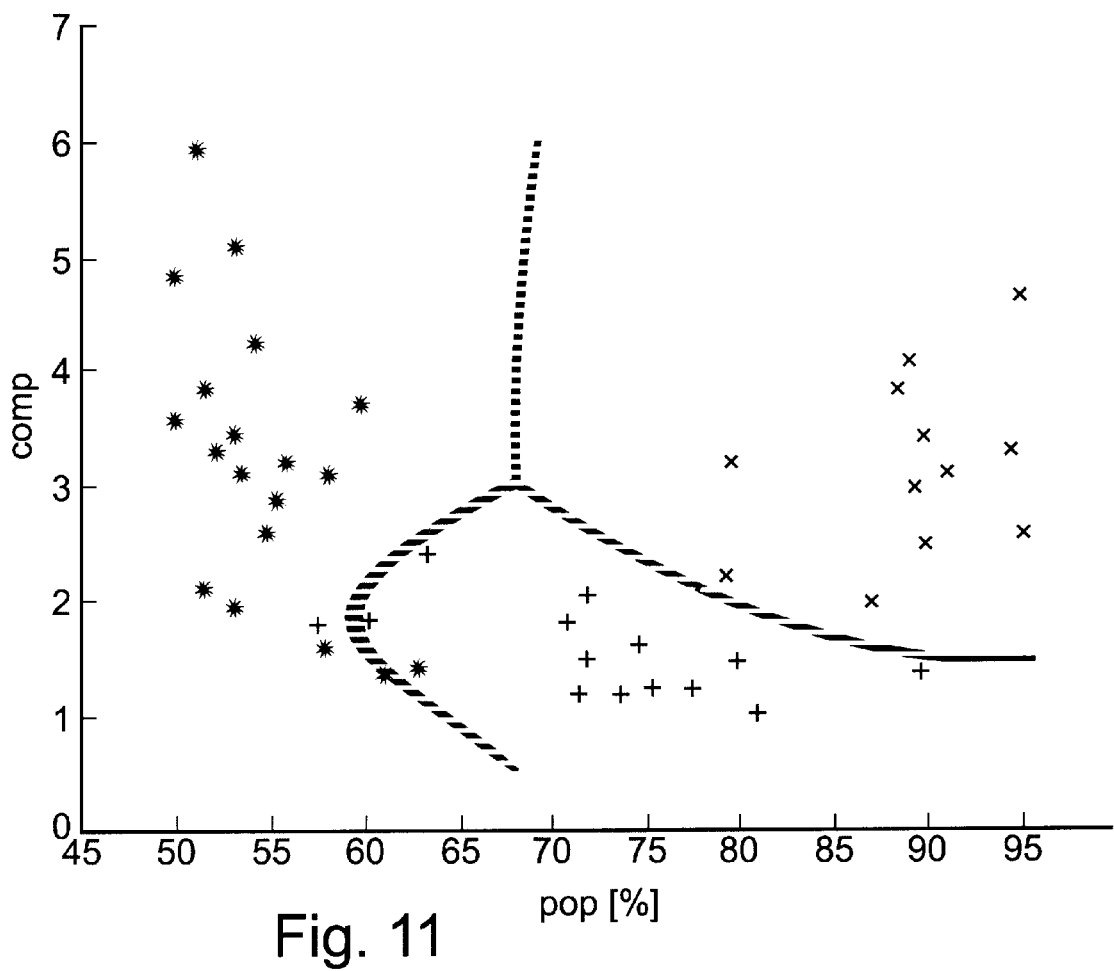
FIG. 11 shows the partition feature space obtained from minimum error rate classification using a training group to train the algorithm according to the present invention. Each structure in the training sample set is described by a symbol in the Figure, wherein a papillation is indicated by a '+', a septation is indicated by a 'x', and a side is indicated by a '*'. When displayed in feature space, the training group forms three clusters. As a result of training, the feature space is divided into three regions (related to papillations, septations and sides). The boundaries between them are illustrated by the curves.

Structure classification: The features (pop, comp) of each structure (excluding complete septations) were computed in order to apply the bivariate analysis. From the set of obtained structures, a group of 47 structures (including 14 papillations, 12 incomplete septations, and 21 sides) was selected as a training set. All members of this set exhibited the characteristic (i.e., "classical") appearance of the associated structures. As shown in FIG. 11, the training set is described by three clusters. The curves divide the feature space into three parts (related to papillations, septations and sides) according to the results obtained from analyzing the training data set.

The bivariate classification technique was tested on 46 papillations, nine incomplete septations and 41 sides. The algorithm classified correctly 33 papillations (representing 71.7% of the tested ones), seven septations (representing 77.8% of the cases) and 37 sides (representing 90.2% of the examined sides). The univariate classification algorithm was tested on one "internal" papillation and seven "internal" septations. The papillation and five of the septations (71.4%) were identified correctly. Combining these results with those obtained using the bivariate algorithm shows correct classification of 72.3% of the papillations (34 of 47 cases), 75% of the septations (12 of 16 cases), and 90.2% of the sides (37 of 41 cases).

For structures of a specific type, correct classification can be regarded "positive" while misclassification regarded "negative". Then, the success rate is in fact the sensitivity of the classification technique for this structure type. Similarly, the specificity, positive predictive value (PPV) and negative predictive value (NPV) of the algorithm can be computed for each structure type. The obtained results are presented in Table 2.

TABLE 2

The performance of structure classification

| Structure type | No. of cases | sensitivity‡ (%) | specificity (%) | PPV‡ (%) | NPV‡ (%) |
|---|---|---|---|---|---|
| Papillation | 47 | 72.3 | 89.5 | 85.0 | 79.5 |
| Incomplete septation | 16 | 75.0 | 94.3 | 70.6 | 95.4 |
| Side | 41 | 90.2 | 84.1 | 78.7 | 93.0 |

†including "internal" structures;
‡the sensitivity equals the success rate;
PPV = Positive Predictive Value; and
NPV = Negative Predictive Value.

Quantitative Analysis:

A quantitative analysis was performed on 61 cases (including: 40 papillations, 18 incomplete septations, one "internal" papillation, and two "internal" septations) which were correctly classified and for which manual measurements were available. This data set contained structures from both groups (training, test) of the above analysis. The values obtained for each structure were then translated from pixels to millimeters, using the calibration data provided by the scanner. For the papillations (including the "internal" ones), the mean difference between the manual and the automatic values of the mean diameter (obtained by averaging absolute differences) was 1.7 mm. For the septations (incomplete and "internal"), this difference between manual and automatic measures for the septation width was 0.9 mm. It appears that the error obtained for papillations is much larger than the one obtained for septations. This is not surprising, since the morphological algorithm is more suited to measure the shortest dimension (i.e., width) of an object rather than to measure its mean diameter.

The proposed technique for computing the width of a complete septation was tested on 48 cases, and the results were compared to manual evaluations. The mean difference obtained between manual and automatic evaluations was 0.9 mm. This result, as well as the values obtained for papillations and incomplete septations, are presented in Table 3 below. Combining the values obtained for the various structure types, one can conclude that the characteristic dimension of a cystic structure obtained by the algorithm described herein matches manual evaluation to within 1–2 mm.

TABLE 3

The performance of quantitative analysis

| structure type | No. of cases | mean error: (mm) |
|---|---|---|
| papillation† | 41 | 1.7 |
| incomplete septation† | 20 | 0.9 |
| complete septation | 48 | 0.9 |

†including "internal" structures;
‡the mean difference between manual and automatic evaluations Structure Classification—Summary:

Table 2 above shows that a success rate of approximately 75% was obtained for structure classification (to be precise, 72.3% for papillations and 75% for incomplete septations). It is believed that this result indicates that the classification algorithm performs reasonably and thus has a promising potential for clinical use. Evidently, there are no similar automatic algorithms with which to compare.

Although the obtained results are satisfactory, a slightly different classification approach may be considered. This commonly used approach allows to reject a data point which is unrecognizable (forming in the present case four structure types, namely: "papillation", "septation", "side" and "rejected"). Borderline cases can then be included in the analysis. Furthermore, the size of the rejection region in feature space (i.e., the region related to the "rejected" structures) can be determined according to the level of confidence desired for classification.

It should be noted that a large number of small structures (papillations and septations) was missed due to the restriction on the structure size employed. However, for such small structures (less than 1% of the cyst), the morphological differences between the three structure types (papillations, septations and sides) become blurred, and this yields a large number of false positives (sides misclassified as papillations or septations). Furthermore, such small structures are usually of little or no medical importance.

Quantitative Analysis—Summary:

It was found that the characteristic dimension of a cystic structure computed by the algorithm agrees with manual evaluation to within 1–2 mm. This resolution is more than reasonable considering the fact that commonly used scoring systems [2, 5, 6] employ a single threshold of 3 mm in order to separate small cystic structures (both papillations and septations) from large ones. Hence, the quantitative technique described herein is satisfactory and presents a good match with manual evaluations.

Automatic boundaries extraction, e.g., segmentation of the image, performed prior to operating algorithm described under this Example, can provide the boundary of cyst and replace the manual tracing applied in this Example. Segmentation of medical images has been widely discussed in the literature. An automatic thresholding technique, especially designed to segment ultrasound images, is described in Example 1 hereinabove and in [15]. Combining automatic segmentation with the algorithm described herein for structure analysis can lead to an automatic morphological analysis of ovarian masses.

Thus, in this Example, an algorithm for the quantification of characterizing structures located within ovarian cysts is described. This algorithm categorizes automatically the various structures within a cyst and extracts their quantitative properties. The obtained results were compared to human classification and manual measurements made by an expert.

When applied to routinely available ultrasound images, the qualitative analysis (i.e., structure classification) succeeded in about 75% of the cases. The quantitative analysis provided a characteristic dimension that agrees with manual evaluation to within 1–2 mm. It is concluded that the algorithm performs well and enables a reliable analysis of the examined structures, thus having a potential for clinical use. Combining the proposed algorithm with a segmentation technique on one hand and with a scoring system on the other can provide an automatic solution for the analysis of ovarian masses.

Example 3

The Convex Hull

The convex hull of a shape is the smallest convex object that contains the original shape. The area added to the original shape (i.e., the difference between the original object and its convex hull) is called the convex deficiency. The convex hull is extensively discussed in the literature, and numerous algorithms have been proposed in order to compute it. A variety of algorithms for finding the convex hull of a finite set of points in the plan is summarized by Preparata and Shamos [31] and Day [32]. Although a shape in a binary image can be viewed as a finite set of points (located at the centers of the pixels), relatively few techniques addressed the convex hull in images.

The upper convex hull (U-hull) of a digital planar object is composed of straight segments bounding the object from above. Similarly, its lower convex hull (L-hull) is composed of straight segments bounding it from beneath. The complete convex hull of the shape can be obtained by combining the U-hull with the L-hull. Andrew's modification of Graham's algorithm [33] is based on this idea, and a similar notion is used by Bentley et al. [34]. However, these algorithms and others apply complex techniques in order to move from point to point along the upper (or the lower) convex hull.

It is proposed herein to simplify the algorithm for finding the U-hull and the L-hull (and hence the convex hull itself). Initially, the rectangle bounding the original object is found. Then, this region is scanned column after column and the uppermost and lowermost object pixels in each column are separately collected. Next, every pair of upper boundary points are connected with a straight segment, and a list of all the points on those segments is constructed. A similar list is generated from the lower boundary points of the object.

When the first list is sorted according to columns, the uppermost point in each column belongs to the U-hull (since the U-hull is the upper bound of the segments represented in that list). Similarly, the set of lowermost points in the sorted second list belongs to the L-hull. Finally, the convex hull itself is obtained by filling all the pixels between the U-hull and the L-hull in each column.

The proposed method is simpler than similar techniques and therefore easier to implement. Furthermore, it uses only part of the boundary points for computation; for an image containing N×N pixels, the maximal number of employed boundary points is 2N. An example of the result obtained used this method is presented in FIGS. 8a–b.

Example 4

Mathematical Morphology

Mathematical morphology is a mathematical technique based on set theory, which provides a quantitative description of geometrical objects and structures. Morphological operations are performed on the object using a moving shape called "structuring element". Implementations of mathematical morphology in image processing have been extensively described in the literature.

The two simplest morphological operations are erosion and dilation. In the binary case, the erosion of an object X by a structuring element B is defined as the group of translations of B that are completely included in X, and the dilation of an object X by a structuring element B is defined as the group of translations of B that are at least partly included in X.

In practice, a mask (whose shape defines the structuring element) is moved from pixel to pixel in the image; a pixel belongs to the eroded image if all the pixels covered by the mask (when the mask is centered on the examined pixel) belong to the object (i.e., have a value "1"). Similarly, a pixel belongs to the dilated pixel if at least one pixel under the mask belongs to the object. Morphological opening of an object means erosion followed by dilation, and morphological closing of an object means dilation followed by erosion.

When the image is eroded using a roundly shaped structuring element (a disc), a pixel belongs to the eroded image only when all pixels within a radius r around it (r being the radius of the structuring element) belong to the object. Similarly, a pixel belongs to the dilated image only when at least one object pixel is found within a distance r from it. When erosion with a disc of radius r is applied on the results of dilation with the same structuring element, morphological closing of the image with this disc is obtained.

Example 5

Minimum Error Rate Classification

Suppose that a region, which is represented in the feature space by a n-dimensional vector x, belongs to one of J classes. According to Bayes rule [16]:

$$P(j/x) = \frac{P(x/j) \cdot P(j)}{P(x)} \quad (20)$$

where P(j) is the a priori probability; and P(j/x)=the a p probability.

Using the well known minimum error rate classifier [16], the vector x belongs to the class j for which P(j/x) is maximized. Obviously, P(x) remains the same for all classes. Furthermore, P(j) is determined as 1/j for all classes due to lack of a priori information. Hence, the vector x is classified by finding the class for which the conditional probability P(x/j) is maximized.

One can easily identify P(x/j) as the probability density of class j, since it provides the probability of having a general vector x in class j. Assuming that P(x/j) is multivariate normal for each class j, one can write:

$$P(x/j) = \frac{1}{(2\pi)^{\frac{n}{2}} |\Sigma_j|^{\frac{1}{2}}} \cdot \exp\left[-\frac{1}{2}(x-\mu_j)^t \sum_j^{-1}(x-\mu_j)\right] \quad (21)$$

where $\mu_j$ is the mean vector; and $\Sigma_j$=the covariance matrix.

A general solution can be obtained by finding where in the feature space each probability density is larger than all others. This partition of the feature space into regions can be also performed using the logarithm of P(x/j), where:

$$\ln[P(x/j)] = -\frac{1}{2}(x-\mu_j)^t \sum_j^{-1}(x-\mu_j) - \frac{n}{2}\ln(2\pi) - \frac{1}{2}\ln\left(\left|\sum_j\right|\right). \quad (22)$$

Omitting the constant term n/2 ln(290), one can now say that a vector x belongs to class j if the following expression:

$$F_k = (x-\mu_k)^t \Sigma_{k-1}(x-\mu_k) + \ln(|\Sigma_k|) \quad (23)$$

where k=1, 2, . . . , J is minimal for the class j.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES CITED

1. Fleischer A C, Romero R, Manning F A, Jeanty P, James A E. The principles and practice of sonography in obstetrics and gynecology. Norwalk, Conn.: Appelton & Lange, 1991, 4 th ed., ch. 35, p. 550.
2. Sassone A M, Timor-Tritsch I, Artier A, Westhoff C, Warren W B. Transvaginal sonographic characterization of ovarian disease: evaluation of a new scoring system to predict ovarian malignancy. Obstet Gynecol 1991;78:70–76.
3. Finkler N J, Benacerraf B, Lavin P T, Wojciechowski C, Knapp R C. Comparison of serum CA 125, clinical impression, and ultrasound in the preoperative evaluation of ovarian masses. Obstet Gynecol 1988;72:659–664.
4. Kurjak A, Predanic M. New scoring system for prediction of ovarian malignancybased on transvaginal color doppler sonography. J Ultrasound Med 1992;11:631–638.
5. DePriest P D, Van Nagell J R, Gallion H H, Shenson D, Hunter J E, Andrews S J, Powell D E, Pavlik E J. Ovarian cancer screening in asymptomatic postmenopausal women. Gynecologic Oncology 1993;51:205–209.
6. Lerner J P, Timor-Tritsch I E, Federman A, Abramovich G. Transvaginal ultrasonographic characterization of ovarian masses with an improved, weighted scoring system. Am. J Obstet Gynecol 1994;170:81–85.
7. Muzzolini R, Yang Y H, Pierson R. Multiresolution texure segmentation with application to diagnostic ultrasound images. IEEE Trans Med Imaging 1993;12:108–123.
8. Muzzolini R, Yang Y H, Pierson R. Texture characterization using robust statistics. Pattern Recog 1994;27:119–134.
9. Muzzolini R, Yang Y H, Pierson R. Classifier design with incomplete knowledge. Pattern Recog 1998;31:345–369.
10. Sarty G E, Liang W, Sonka M, Pierson R A. Semiautomated segmentation of ovarian follicular ultrasound images using a knowledge-based algorithm. Ultrasound Med Biol 1998;24:27–42.
11. Potocnic B, Zazula D, Korze D. Automatic computer-assisted detection of follicles in ultrasound images of ovary. Proc. of the Tenth IEEE Symposium on Computer-Based Medical Systems, Jun. 11–13, 1997, Maribor, Slovenia, pp. 16–21.
12. Viher B, Dobnikar A, Zazula D. Follicle recognition in ultrasound images using the cellular automata. Proc. of the Tenth IEEE Symposium on Computer-Based Medical Systems, Jun. 11–13, 1997, Maribor, Slovenia, pp. 34–39.
13. Brüning J, Becker R, Entezami M, Loy V, Vonk R, Weitzel H, Tolxdorff T. Knowledge-based system ADN-EXPERT to assist the sonographic diagnosis of adnexal tumors. Methods Inf Med 1997;36:201–206.
14. L i C H, Lee C K. Minimum cross entropy thresholding. Pattern Recognition 1993;26:617–625.
15. Zimmer Y, Tepper R, Akselrod S. A two dimensional extension of minimum cross entropy thresholding for the segmentation of ultrasound images. Ultrasound Med Biol 1996;22:1183–1190.
16. Duda R O, Hart PE. Pattern classification and scene analysis. New-York: John Wiley & Sons, 1973, ch. 2.
17. Muzzolini R, Yang Y H, Pierson R. Multiresolution texture segmentation with application to diagnostic ultrasound images. IEEE Trans Med Imaging 1993;12:108–123.
18. Muzzolini R, Yang Y H, Pierson R. Texture characterization using robust statistics. Pattern Recognition 1994;27:119–134.
19. Shinozuka N, Oye Y, Yamakoshi Y, Taketani Y. Transvaginal sonographic orientation detection system using ceramic gyroscopes. J Ultrasound Med 1996;15:107–113.
20. Kittler J, Illingworth J. Minimum error thresholding. Pattern Recognition 1986;19:41–47.
21. Otsu N. A threshold selection method from gray-level histogram. IEEE Trans Syst Man Cybern 1979;9:62–66.
22. Kapur J N, Sahoo P K, Wong A K C. A new method for gray-level picture thresholding using the entropy of the histogram. Comput Vision Graphics Image Process 1985;29:273–285.
23. Li C H, Lee C K. Minimum cross entropy thresholding. Pattern Recognition 1993;26:617–625.
24. Brink A D, Pendock N E. Minimum cross entropy threshold selection. Pattern Recognition 1996;29:179–188.
25. Abutaleb A S. Automatic thresholding of gray-level pictures using two dimensional entropy. Comput Vision Graphics Image Process 1989;47:22–32.
26. Brink A D. Thresholding of digital images using two-dimensional entropies. Pattern Recognition 1992;25:803–808.
27. Crawford D C, Bell D S, Bamber J C. Compensation for the signal processing characteristics of ultrasound B-mode scanners in adaptive speckle reduction. Ultrasound Med Biol 1993;19:469–485.
28. Karaman M, Kutay M A, Bozdagi G. An adaptive speckle suppression filter for medical ultrasonic imaging. IEEE Trans Med Imaging 1995;14:283–292.
29. Kullback S. Information theory and statistics. New York: Wiley, 1959.
30. Jain A K. Fundamentals of digital image processing. Englewood Cliffs, New Jersey: Prentice Hall, 1989.
31. Preparata F P, Shamos M I. Computational geometry: an introduction. New-York: Springer-Verlag, 1985, 2nd ed., ch. 3–4.
32. Day A M. Planar convex hull algorithms in theory and practice. Computer Graphics Forum 1988;7:177–193.
33. Andrew A M. Another efficient algorithm for convex hulls in two dimensions. Information Processing Letters 1979;9:216–219.
34. Bentley J L, Faust M G, Preparata F P. Approximation algorithms for convex hulls. Comm of the ACM 1982;25:64–68.
35. Cho Z H, Jones J P, Singh M. Foundations of medical imaging. New York: John Wiley & Sons, 1993.
36. Ballard D H, Brown C M. Computer vision. Englewood Cliffs, New Jersey:Prentice-Hall, 1982.
37. Blake A, Yuille A (eds.). Active vision. Cambridge Massachusetts: The MIT Press, 1992.
38. Chu C H, Delp E J, Buda A J. Detecting left ventricular endocardial and epicardial boundaries by digital two-dimensional echocardiography. IEEE Trans. Med. Imaging, 1988;7:81–90.
39. Sahoo P K, Soltani S, Wong A K C. A survey of thresholding techniques. Comput. Vision Graph. Image Proc. 1988;41:233–260.

What is claimed is:

1. A method of characterizing an adnexal mass, the method comprising the steps of:
(a) obtaining an ultrasound image of an examined adnex including the adnexal mass;
(b) extracting boundaries of said adnexal mass using a first algorithm selected from the group consisting of an edge extraction algorithm and a region extraction algorithm; and
(c) using a second algorithm for:
(i) classifying said adnexal mass to a cyst, a solid mass or a semi-solid mass; and
(ii) quantifying at least one morphological feature of said adnexal mass, said at least one morphological feature of said adnexal mass is selected from the group consisting of size, volume, presence of papillations, presence of septations, wall regularity, turbidity, homogeneity and echogenic foci, thereby providing quantification of said at least one morphological feature.

2. The method of claim 1, wherein said ultrasound is selected from the group consisting of B scan ultrasound and Doppler ultrasound.

3. The method of claim 1, wherein extracting said boundaries of said adnexal mass is effected manually.

4. The method of claim 1, wherein said edge extraction algorithm is selected from the group consisting of an active contour model algorithm, a radial search algorithm and a contour following algorithm.

5. The method of claim 1, wherein said region extraction algorithm is selected from the group consisting of a region growing algorithm and a thresholding algorithm.

6. The method of claim 1, further comprising the step:
(d) using said quantification of said at least one morphological feature of said adnexal mass in a scoring system for issuing a diagnosis related to said adnexal mass.

7. The method of claim 1, wherein said scoring system is effected by a third algorithm.

8. The method of claim 1, wherein said scoring system is effected manually.

9. A system of characterizing an adnexal mass comprising:
(a) a first hardware for operating a first algorithm for obtaining an ultrasound image of an examined adnex including the adnexal mass in a digitized form;
(b) a second hardware for operating a second algorithm for:
(i) classifying said adnexal mass to a cyst, a solid mass or a semi-solid mass; and
(ii) quantifying at least one morphological feature of said adnexal mass, said at least one morphological feature of said adnexal mass is selected from the group consisting of size, volume, presence of papillations, presence of septations, wall regularity, turbidity, homogeneity and echogenic foci, thereby providing quantification of said at least one morphological feature; and
(c) a third hardware for operating a third algorithm for extracting boundaries of said adnexal mass selected from the group consisting of an edge extraction algorithm and a region extraction algorithm.

10. The system of claim 9, wherein said ultrasound is selected from the group consisting of B scan ultrasound and Doppler ultrasound.

11. The system of claim 9, wherein said edge extraction algorithm is selected from the group consisting of an active contour model algorithm, a radial search algorithm and a contour following algorithm.

12. The system of claim 9, wherein said region extraction algorithm is selected from the group consisting of a region growing algorithm and a thresholding algorithm.

13. The system of claim 9, further comprising:
(e) a fourth hardware for operating a scoring algorithm for issuing a diagnosis related to said adnexal mass based on said quantification of said at least one morphological feature of said adnexal mass.

* * * * *

UNITED STATES PATENT AND TRADEMARK OFFICE
CERTIFICATE OF CORRECTION

PATENT NO. : 6,858,007 B1
DATED : February 22, 2005
INVENTOR(S) : Solange Akselrod et al.

It is certified that error appears in the above-identified patent and that said Letters Patent is hereby corrected as shown below:

Column 4,
Line 34, change "FIG 2 show" to -- FIG 2 shows --.

Column 7,
Line 44, change "active 5 contour" to -- active contour --.
Line 55, change "but no" to -- but not --.

Column 9,
Line 41, change "pan be" to -- can be --.

Column 11,
Line 39, change "comedical" to -- context of medical --.

Column 12,
Line 40, change "$h_j = $ the" to -- $h_j = $ the --.

Column 13,
Line 10, change "$K_2(i,j) = \sqrt{i^2 + 30j^2}$" to -- $K_2(i,j) = \sqrt{i^2 + j^2}$ --.

Line 56, change "$K_2(i,j) = \sqrt{a^2 i^2 + 30 b^2 j^2}$" to -- $K_2(i,j) = \sqrt{a^2 i^2 + b^2 j^2}$ --.

Column 15,
Line 12, change "The later" to -- The latter --.

Column 17,
Line 60, change "of 15 ovarian" to -- of ovarian --.

Column 22,
Line 1, change " $F_k = (x - \mu_k)^t \phantom{}_k^{-1}(x - \mu_k) + \ln(|\Sigma_k|)$ " to
-- $F_k = (x - \mu_k)^t \Sigma_k^{-1}(x - \mu_k) + \ln(|\Sigma_k|)$ --.

Column 27,
Line 18, change "=the a p" to -- =the a priori --.
Line 34, change "$\Sigma^{-1}_j$" to -- $\Sigma^{-1}_j$ --.

UNITED STATES PATENT AND TRADEMARK OFFICE
CERTIFICATE OF CORRECTION

PATENT NO. : 6,858,007 B1
DATED : February 22, 2005
INVENTOR(S) : Solange Akselrod et al.

It is certified that error appears in the above-identified patent and that said Letters Patent is hereby corrected as shown below:

Column 27 (cont'd),

Line 44, change "$\sum_{j}^{-1}$" to -- $\sum_{j}^{-1}$ --.

Line 48, change "n/2 1n(290)" to -- n/2 1n(2π) --.

Signed and Sealed this

Eighteenth Day of October, 2005

JON W. DUDAS
*Director of the United States Patent and Trademark Office*